(12) United States Patent
Powers et al.

(10) Patent No.: US 10,021,747 B2
(45) Date of Patent: Jul. 10, 2018

(54) HIGH POWER, SINUSOIDAL LED DRIVER WITH TEMPERATURE STABILIZATION FEEDBACK AND PHOTOMULTIPLIER SYSTEM

(71) Applicant: ARIZONA BOARD OF REGENTS ON BEHALF OF THE UNIVERSITY OF ARIZONA, Tucson, AZ (US)

(72) Inventors: Linda S. Powers, Tucson, AZ (US); Jerrie V. Fairbanks, Tucson, AZ (US); Janet M. Roveda, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 15/827,989

(22) Filed: Nov. 30, 2017

(65) Prior Publication Data
US 2018/0092177 A1   Mar. 29, 2018

Related U.S. Application Data

(63) Continuation-in-part of application No. 15/431,319, filed on Feb. 13, 2017, now Pat. No. 9,867,250, which is a continuation-in-part of application No. 15/134,000, filed on Apr. 20, 2016.

(60) Provisional application No. 61/150,167, filed on Apr. 20, 2015.

(51) Int. Cl.
*H03K 5/01* (2006.01)
*H05B 33/08* (2006.01)
*H03K 5/08* (2006.01)

(52) U.S. Cl.
CPC ........... *H05B 33/0824* (2013.01); *H03K 5/08* (2013.01); *H05B 33/0812* (2013.01); *H05B 33/0815* (2013.01); *H05B 33/0893* (2013.01)

(58) Field of Classification Search
CPC combination set(s) only.
See application file for complete search history.

(56) References Cited

U.S. PATENT DOCUMENTS

| | | |
|---|---|---|
| 3,992,631 A | 11/1976 | Harte |
| 4,133,639 A | 1/1979 | Harte |
| 4,939,443 A | 7/1990 | Pollmeier et al. |
| 5,512,492 A | 4/1996 | Herron et al. |

(Continued)

OTHER PUBLICATIONS

Ulrich, H. et ai, Journal of Biological Chemistry 2002, 277, 20756-20762.

(Continued)

*Primary Examiner* — Monica C King
*Assistant Examiner* — Jianzi Chen
(74) *Attorney, Agent, or Firm* — Nguyen & Tarbet Law Firm

(57) ABSTRACT

A high intensity, ultra-short LED pulsing driver circuit is developed for use with a system designed to perform real-time time-resolved, transient recording of fluorescence. Details of the timing circuitry used to pulse the LED and to provide synchronized PMT gating and ADC trigger pulses are also developed. The LED pulses are intended for fluorophores with lifetimes on the order of about 1.6 ns or longer and gating is used to maintain the detector off or partially off during excitation, thereby maximizing the available detector gain without saturation of the detector by the excitation light.

20 Claims, 13 Drawing Sheets

(56) References Cited

U.S. PATENT DOCUMENTS

| | | | |
|---|---|---|---|
| 5,573,909 | A | 11/1996 | Singer et al. |
| 5,646,001 | A | 7/1997 | Terstappen et al. |
| 5,760,406 | A | 6/1998 | Powers |
| 5,968,766 | A | 10/1999 | Powers |
| 6,121,053 | A | 9/2000 | Kolber et al. |
| 6,391,578 | B2 | 5/2002 | Williams et al. |
| 6,518,068 | B1 | 2/2003 | Gambini et al. |
| 6,582,903 | B1 | 6/2003 | Rigler et al. |
| 6,649,403 | B1 | 11/2003 | McDevitt et al. |
| 6,750,006 | B2 | 6/2004 | Powers et al. |
| 6,780,602 | B2 | 8/2004 | Powers et al. |
| 6,790,611 | B2 | 9/2004 | Lassen et al. |
| 6,797,463 | B2 | 9/2004 | Abbott et al. |
| 6,846,639 | B2 | 1/2005 | Miles et al. |
| 7,079,241 | B2 | 7/2006 | Empedocles et al. |
| 7,112,773 | B2 | 9/2006 | Thompson |
| 7,186,990 | B2 | 3/2007 | Powers et al. |
| 7,211,377 | B1 | 5/2007 | Powers et al. |
| 7,289,207 | B2 | 10/2007 | Grace et al. |
| 7,824,883 | B2 | 11/2010 | Powers et al. |
| 2002/0045272 | A1 | 4/2002 | McDevitt et al. |
| 2002/0150886 | A1 | 10/2002 | Miles et al. |
| 2003/0003441 | A1 | 1/2003 | Colston et al. |
| 2003/0124532 | A1 | 7/2003 | Powers et al. |
| 2003/0138875 | A1 | 7/2003 | Powers et al. |
| 2003/0170613 | A1 | 9/2003 | Straus |
| 2004/0063160 | A1 | 4/2004 | Lassen et al. |
| 2004/0197771 | A1 | 10/2004 | Powers et al. |
| 2005/0088648 | A1 | 4/2005 | Grace et al. |
| 2005/0112557 | A1 | 5/2005 | Liu et al. |
| 2005/0250141 | A1 | 11/2005 | Lambert et al. |
| 2005/0266398 | A1 | 12/2005 | Lea et al. |
| 2006/0257929 | A1 | 11/2006 | Powers et al. |
| 2008/0032327 | A1 | 2/2008 | Powers et al. |
| 2008/0241858 | A1 | 10/2008 | Metzger et al. |
| 2008/0262321 | A1 | 10/2008 | Erad et al. |
| 2008/0311590 | A1 | 12/2008 | Tan et al. |
| 2009/0017476 | A1 | 1/2009 | Tan et al. |
| 2009/0087867 | A1 | 4/2009 | Ono et al. |
| 2010/0184103 | A1 | 7/2010 | Jing et al. |
| 2010/0285490 | A1 | 11/2010 | Dees et al. |
| 2013/0221869 | A1 | 8/2013 | Volk et al. |
| 2015/0268244 | A1 | 9/2015 | Cho et al. |
| 2016/0097763 | A1 | 4/2016 | Powers et al. |

OTHER PUBLICATIONS

Banani, N. et ai, Proceedings of the 26th Annual International Conference of the IEEE EMBS 2004, 2096-2089.
Torres-Chavolla, E. et ai, Biosensors and Bioelectronics 2009,24,3175-3182.
Powers, L. S. et ai, Journal of Biosensors and Bioelectronics 2012, S11, paper 001,6 pages.
G. F. Knoll, "Scintillation detector principles," in Radiation Detection and Measurement, 2nd ed., New York, Wiley, 1989, ch. 8, pp. 215-250.
J. R. Lakowicz, "Time-domain lifetime measurements," in Principles of Fluorescence Spectroscopy, 3rd ed. New York, Springer, 2006, ch. 4, sec. 4.8.1, pp. 63-64, 97-155.
J. R. Lakowicz, "Introduction to fluorescence," in Principles of Fluorescence Spectroscopy, 3rd ed., New York, Springer, 2006, ch. 1, sec. 1.2, pp. 5.
M. Hof et al., "Basics of fluorescence spectroscopy in biosciences," in Fluorescence Spectroscopy in Biology: Advanced methods and their applications to membranes, proteins, DNA, and cells, ser. 3, Berlin Heidelberg, Germany, 2005, ch. 1, sec. 1.2.1, pp. 4-5.
J. R. Albani, "Fluorescence spectroscopy principles," in Principles and Applications of Fluorescence Spectroscopy, 1st ed. Oxford, UK, Blackwell, 2007, ch. 7, sec. 7.2.7.1, pp. 94-97.
J. R. Lakowicz, "Introduction to fluorescence," in Principles of Fluorescence Spectroscopy, 3rd ed. New York, Springer, 2006, ch. 1, sec. 1.9.4, pp. 18-19.
J. D. Mycek M-A, "Design and development of a rapid acquisition laser-based fluorometer with simultaneous spectral and temporal resolution," in Rev. Sci. Instrum., vol. 72, pp. 3061-3072, 2001.
J. R. Lakowicz, "Frequency-domain lifetime measurements," in Principles of Fluorescence Spectroscopy, 3rd ed. New York, Springer, 2006, ch. 5, sec. 5.1 pp. 157-160.
R. Wardle, "Gating of photomultipliers," ET Enterprises, Uxbridge, UK, Rep. R/P061, 2011.
A. E. Moe et al., "Improvements in LED-based fluorescence analysis systems," Sens. Actuators B, No. 111-112, pp. 230-241, Apr. 2005.
B. R. Rae et al., , "A vertically integrated CMOS microsystem for time-resolved fluorescence analysis," in IEEE Trans. Biomed. Circuits Syst., vol. 4, No. 6, pp. 437-444, Dec. 2010.
J. E. Dickens et al., "An LED array-based light induced fluorescence sensor for real-time process and field monitoring", in Sensors and Actuators, vol B, No. 158, pp. 35-42, 2011.
A. R. Boutonnet et al., "A comparative study of LED-induced fluorescence and laser induced fluorescence in SDS-CGE: Application to the analysis of antibodies," in Electrophoresis, vol. 33, pp. 1709-1714, 2012, (doi: 10.1002/elps.201200132).
H. Wang et al., , "A portable time-domain LED fluorimeter for nanosecond fluorescence lifetime measurements," Review of Scientific Instruments, vol. 85, No. 055003, 2014, (doi: 0.1063/1.4873330).
Q. Fang et al., "Time-domain laser-induced fluorescence spectroscopy apparatus for clinical diagnostics," Review of Scientific Instruments, vol. 75, No. 151, 2004, (doi: 10.1063/1.1634354).
P. Urayama, "A UV-Visible-NIR fluorescence lifetime imaging microscope for laser-based biological sensing with picosecond resolution," Appl. Phys. B, No. 76, pp. 483-496, Feb. 2003, (doi: 10.1007/s00340-003-1152-4).
J. Requejo-Isidro et al., "High-speed wide-field time-gated endoscopic fluorescence-lifetime imaging," Optics Letters, vol. 29, No. 19, pp. 2249-2251, 2004.
B. B. Collier, "Time-resolved measurements of luminescence," in Journal of Luminescence, vol. 144, pp. 180-190, 2013.
M. Wahl et al., , "Integrated multichannel photon timing instrument with very short dead time and high throughput," Review of Scientific Instruments, vol. 84, No. 043102, 2013, (doi: 10.1063/1.4795828).
S. Antonioli et al., "8-channel acquisition system for time-correlated single-photon counting," Review of Scientific Instruments, vol. 84, No. 064705, 2013, (doi: 10.1063/1.4811377).
K. J. Petersen et al., "Fluorescence lifetime plate reader: Resolution and precision meet high-throughput," Review of Scientific Instruments, vol. 85, No. 113101, 2014, (doi: 10.1063/1.4900727).
C. Estes et al., "Reagentless detection of microorganisms by intrinsic fluorescence," in Biosensors and Bioelectronics, vol. 18, No. 5-6, pp. 511-519, May 2002 & May 2003 (Selected papers from the Seventh World Congress on Biosensors, Kyoto, Japan 15-17).
A. Duncan and L. Powers, "Low noise amplification for optical arrays," in Proc. 23rd Annu. Int. Conf. IEEE Eng. Med. Biol. Mag., Istanbul, Turkey, Oct. 25-28, 2001.
A. Duncan and L. Powers, "Array-based design of multi-wavelength fluorescence system," in Proc. 23rd Annu. Int. Conf. IEEE Eng. Med. Biol. Mag., Istanbul, Turkey, Oct. 25-28, 2001.
C. Lloyd et al., "Microbioengineering: microbe capture and detection," in Proc. 23rd Annu. Int. Conf. IEEE Eng. Med. Biol. Mag., Istanbul, Turkey, Oct. 25-28, 2001.
B. Wade et al., "Algorithm for recognition of optical spectra in an environment containing interferants," in Proc. 23rd Annu. Int. Conf. IEEE Eng. Med. Biol. Mag., Istanbul, Turkey, Oct. 25-28, 2001.
H.-Y. Kim et al., "Real-time detection of microbial contamination," in IEEE Eng. Med. Biol. Mag., vol. 23, pp. 122-129, 2004.
A. P. Kilungo et al., "Continuous real-time detection of microbial contamination in water using intrinsic fluorescence," J Biosens Bioelectron, ser. 12, vol. 002, 2013. (doi:10.4172/2155-6210.S12-002).
J. V. Fairbanks et al., "Fluorescent decay measurements using high speed electronics," J Biosens Bioelectron, ser. 11, vol. 003, 2013. (doi: 10.4172/2155-6210.S11-003).

(56) References Cited

OTHER PUBLICATIONS

K. Kalyanasundaram, "Photophysics, photochemistry and solar energy conversion with tris(bipyridyl)ruthenium(II) and its analogues," Coord Chem Rev, vol. 46, pp. 159-244, 2015.
P. A. Molchanov et. al., "Nanosecond gated PMT for LIDAR-RADAR applications," SPIE Proceedings, vol. 6294, Sep. 2006, (doi: 10.1117/12.675527).
B. Carter, "A current feedback op-amp circuit collection," Texas Instruments Inc., Dallas, TX, Rep. SLOA066, 2001.
Texas Instruments, "1.8-GHz, low distortion, current-feedback amplifier," THS3201 datasheet, Jun. 2003 [Revised Jun. 2009].
J. Olmsted III and D. R. Kearns, "Mechanism of ethidium bromide fluorescence enhancement on binding to nucleic acids," Biochemistry, vol. 16, No. 16, pp. 3647-3654, 1977.
W. Demtröder, "Nonlinear spectroscopy," in Laser Spectronscopy: Basic Concepts and Instrumentation , 3rd ed. New York, Springer, 2003, ch.7, sec. 7.2.1, pp. 446.
A. Einstein, "On the quantum theory of radiation," in Laser Theory, F. A. Barnes, ed., IEEE Press, New York 1972, pp. 5-21.
J. R. Lakowicz, "Time-domain lifetime measurements," in Principles of Fluorescence Spectroscopy, 3rd ed. Berlin, Germany, Springer-Verlag, 2006, ch. 4, sec. 4.8.1 pp. 63-64, 97-155.
K. M. Katika et al., "In vivo time-resolved autofluorescence measurements on human skin," in Proc. SPIE, vol. 6078 Photonic Therapeutics and Diagnostics II, No. 60780L, Feb. 2006. (doi: 10.1117/12.647149; http://dx.doi.org/10.1117/12.647149).
C. D. McGuinness et al., "A new subnanosecond LED at 280nm: application to protein fluorescence," in Meas. Sci. Technol., vol. 15, pp. L19-L22, 2004. (doi: 10.1088/0957-0233/15/11/L02; http://stacks.iop.org/mt/15/L19).
A. S. Sedra and K. C. Smith, "Semiconductors," in Microelectronic Circuits, 6th ed. New York, Oxford Univ., 2010, ch. 3, sec. 3.6, pp. 154-156.
E. F. Schubert, "Radiative and non-radiative recombination," in Light-Emitting Didoes, 2nd ed. Cambridge, UK, Cambridge Univ., 2006, ch. 2, pp. 28-34.
G. F. Franklin et al., "Review of continuous control," in Digital Control of Dynamic Systems, 3rd ed. Half Moon Bay, Ellis-Kagle, 2006, ch. 2, sec. 2.1.7, pp. 20-21.
W. J. O'Hagan et al., "MHz LED source for nanosecond fluorescence sensing," in Meas. Sci. Technol. vol. 13, pp. 84-91, 2002. (doi: 10.1088/0957-0233/13/1/311; http://iopscience.iop.org/0957-0233/13/1/311/).
J. R. Lakowicz, "Time-domain lifetime measurements," in Principles of Fluorescence Spectroscopy, 3rd ed. New York, Springer, 2006, ch. 4, sec. 4.3.1, pp. 104-105.
Analog Devices, "3.3 V Dual-loop 50 Mbps to 1.25 Gbps laser diode driver," ADN2848 datasheet, 2013 [Revision B].
E. F. Schubert, "LED modulation characteristics," in Light-Emitting Didoes, 2nd ed. Cambridge, UK, Cambridge Univ., 2006, ch. 24, pp. 399-400.
P. H. Binh, "Schottky-capacitance pulse-shaping circuit for high-speed light emitting diode operation," in Electronics letters, vol. 48, No. 12, pp. 721-722, 2015.
Texas Instruments, 4.5ns Rail-to-Rail, High-Speed Comparator in Microsize Packages, TLV3501 datasheet, Mar. 2005 [Revised Jul. 2005].
Photomultiplier Tubes: Basics and Applications, 3rd ed. Hamamatsu Co., Hamamatsu, Japan, 2006. pp. 83-123.
U. Farinelli and R. Malvano, "Pulsing of photomultipliers," in Review of Scientific Instruments, vol. 29, No. 8, pp. 699-701, Aug. 1958.
G. M. Hagen et al., "Flexible normally on gating strategy for reducing postgate artifacts," in Review of Scientific Instruments, vol. 76, No. 083117, pp. 1-5, 2005.
Hamamatsu, "Photomultiplier tube R9880U series," R9880U datasheet, 2010.
Photomultiplier Tubes and Assemblies for Scintillation Counting & High Energy Physcics, Hamamatsu Co., Hamamatsu, Japan, 2012.

Y. Kanaya and H. Akimoto, "Gating a channel photomultiplier with a fast high-voltage switch: reduction of afterpulse rates in a laser-induced fluorescence instrument for measurement of atmospheric OH radical concentrations," in Applied Optics, vol. 45, No. 6, pp. 1254-1259, Feb. 2006.
T. M. Yoshida et al., "A highspeed photomultiplier gating circuit for luminescence measurements," in Review of Scientific Instruments, vol. 60, No. 6, pp. 2924-2928, Sep. 1989.
T. Iwata et al., "Combination of a gated photomultiplier tube and a phase sensitive detector for use in an intensive pulse background light situation," in Optical Review, vol. 9, No. 1, pp. 18-24, 2002.
B. L. Elphick, "A method of applying an avalanche transistor generated 70ns gating pulse to a focused photomultiplier," in J. Phys. E, ser. 2, vol. 2, pp. 953-955, 1969.
J. R. Lakowicz, "Fluorophores," in Principles of Fluorescence Spectroscopy, 3rd ed. New York, Springer, 2006, ch. 3, sec. 3.1.1, pp. 63-64.
A. G. Ryder et al., "Evaluation of acridine in nafion as a fluorescence-lifetime-based pH sensor," in Applied Spectroscopy, vol. 57, No. 1, pp. 73-79, 2003.
N. Miyoshi et al., "Fluorescence lifetime of acridine orage in sodium dodecyl sulfate premicullar solutions," in Photochemistry and Photobiology, vol. 47, No. 5, pp. 685-688, 1988.
Y. Kubota and R. F. Steiner, "Fluorescence decay and quantum yield characteristics of acridine orange and proflavine bound to DNA," in Biophysical Chemistry vol. 6, pp. 279-289, 1977.
J. Kapuscinski, "Interactions of nucleic-acids with fluorescent dyes—spectral properties of condensed complexes," in Journal of Histochemistry & Cytochemistry, vol. 38, No. 9, pp. 1323-1329, 1990.
R. G. Baraniuk et al., "Model-based compressive sensing," in IEEE Trans. Inform. Theory, vol. 56, No. 4, pp. 1982-2001, Apr. 2010.
K. M. Okarski, "Novel Point-of-Care Disposable Device and Cell Culture Bioprocessing Technique," Ph.D. dissertation, Biom. Engr. Dept. (GIDP), Univ. of Arizona, Tucson, AZ, 2016.
L. Powers et al., "Read-time in situ detection and quantification of bacteria in the Arctic environment," Journal of Innovative Optical Health Sciences, vol. 7, No. 2, 2014. (doi: 10.1142/S1793545813500387).
E. F. Schubert, "Junction and carrier temperatures," in Light-Emitting Didoes, 2nd ed., Cambridge, UK, Cambridge Univ., 2006, ch. 6, pp. 101-112.
J. Karki, "Active low-pass filter design," Texas Instruments, Dallas, TX, Rep. SLOA049B, 2002.
Photodiode Technical Information, Hamamatsu Co., Hamamatsu, Japan, pp. 6 & 8, 2015.
Blyth CC, Booy R, Dwyer DE: Point of care testing: diagnostics outside the virology laboratory. Meth Mol Biol 615:415-433, 2011.
Moore C: Point-of-care tests for infection control: should rapid testing be in the laboratory or at the front line? J Hosp Infect 85:1-7, 2013.
Mohd Hanafiah K, Garcia M, Anderson D: Point-of-care testing and the control of infectious diseases. Biomark Med 7:333-347, 2013.
Abou Tayoun AN, Burchard PR, Malik I, Scherer A, Tsongalis GJ: Democratizing molecular diagnostics for the developing world. Am J Clin Pathol 141:17-24, 2014.
Fournier-Wirth C, Jaffrezic-Renault N, Coste J: Transfusion of blood-transmissible agents: can screening be miniaturized? Transfusion 50:2032-2045, 2010.
Perkins HA and Busch MP: Transfusion-associated infections: 50 years of relentless challenges and remarkable progress. Transfusion 50:2080-2099, 2010.
Spinella PC, Dunne J, Beilman GJ, O'Connell RJ, Borgman MA, Cap AP, Rentas F: Constant challenges and evolution of US military transfusion medicine and blood operations in combat. Transfusion 52:1146-1153, 2012.
Moor Ace, Dubbelman Tmar, Van Stevenick J, Brand A: Transfusion-transmitted diseases: risks, prevention and perspectives. Eur J Haematol 62:1-18, 1999.
Hillyer CD, Josephson CD, Blajchman MA, Vostel JG, Epstein JS, Goodman JL: Bacterial contamination of blood components: Risks, strategies, and regulation. Hematology 2003:575-589, 2003.

(56) References Cited

OTHER PUBLICATIONS

Cooper JK, Ladhani K, Minor P: Comparison of candidate vCJD in vitro diagnostic assays using identical sample sets. Vox Sang 102:100-109, 2012.

Blevins SM, Greenfield RA, Bronze MS: Blood smear analysis in babesiosis, ehrlichiosis, relapsing fever, malaria, and Chagas disease. Cleveland Clinic J Med 75:521-530, 2008.

HIGH POWER, SINUSOIDAL LED DRIVER WITH TEMPERATURE STABILIZATION FEEDBACK AND PHOTOMULTIPLIER SYSTEM

CROSS REFERENCE

This application is a continuation-in-part and claims benefit of U.S. patent application Ser. No. 15/431,319, filed Feb. 13, 2017, and is a continuation-in-part and claims benefit of U.S. patent application Ser. No. 15/134,000, filed Apr. 20, 2016, which is a non-provisional and claims benefit of U.S. Provisional Application No. 62/150,167, filed Apr. 20, 2015, the specification(s) of which is/are incorporated herein in their entirety by reference.

FIELD OF THE INVENTION

The present invention provides a means for generating and recording the transient behavior of optical signals (e.g. fluorescence). More specifically, a system comprising a photomultiplier tube (PMT), biasing and gating circuitry for the PMT, and a pulsed light emitting diode (LED) driver circuit is presented. The system is effective for generating and recording fluorescent decay signals from fluorophores. The LED driver circuit and LED produce tunable high-intensity, ultra-short, light pulses. The PMT is biased and gaited to capture the optical signal of interest (e.g fluorescence) as a function of time. The timing can be set such that the PMT is on after the LED has turned off, after the LED has turned partially off, or the PMT can be on during the complete LED pulse depending on the application.

BACKGROUND OF THE INVENTION

Fluorescence is one of the physical phenomena where light is emitted by a material as a result of first absorbing light or other electromagnetic radiation. The emitted light typically has a lower energy (longer wavelength) than the light absorbed. Fluorescence is an invaluable measurement tool with applications ranging from mining to biology. In consequence, countless instruments have been constructed to measure various aspects of fluorescence from excited materials. One application of the present invention optimizes the transient recording of fluorescent emissions from biological samples as follows. LED (instead of laser) excitation is used to minimize photochemical effects (i.e. spectral hole burning) and to excite all available fluorophores by matching the absorption spectrum of the fluorophore with the broad spectrum of the LED. Fluorescent lifetime can be determined from the recorded signals. Pluralities of time constants may be indicative of a mixture of a molecule in a plurality of physical states. Information of this nature may be helpful for cancer diagnosis, forensic tissue examination, and other areas of research.

The present invention can further optimize the transient recording of fluorescent emissions by using the gating paradigm of photomultiplier tubes (PMT). The PMT is gated off during LED excitation to avoid PMT saturation allowing for higher intensity LED or laser pulses. This technique has been used abundantly in scintillation counting for high-energy physics [1], but has rarely been used for biological applications. This is because in scintillation counting, the shape of the signal is less important than the total energy and the occurrence of events, but in biology the shape of the signal (initial intensity and time constants/lifetimes) correlates with the fluorophores being excited. Gating introduces significant systematic error that is sometimes difficult to remove and can obscure intensities and lifetimes [2]. However, modern electronics and basic signal processing can greatly enhance the capabilities of these kinds of instruments by increasing speed and reducing systematic error.

Transient properties of fluorophores can also be studied by using sinusoidal excitation and observing the resulting modulations of fluorescence intensity and phase. Modulations in phase and intensity can be used to estimate the fluorescent lifetimes.

LED's can be crafted with a wide range of spectral properties and are of particular interest because their spectral range can be matched to the absorption spectrum of fluorophores. LED output intensity also responds very quickly to changes in current, but due to being semiconductor devices, the relationship between current and intensity is not very linear close to the voltage threshold.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a system effective for time-resolved, transient recording of fluorescent lifetimes. In a broad embodiment, the system comprises:
  a. a personal computer (PC) graphical interface (101), operatively coupled to a microcontroller, wherein the PC (101) initiates a series of pulses from the microcontroller (102), the PC (101) and microcontroller (102) collectively referred to as a microcontroller edge trigger;
  b. the microcontroller (102);
  c. a light emitting diode (LED) pulsing driver circuit (300), operatively connected to an LED (304), triggered by the microcontroller edge trigger, the LED pulsing driver circuit comprising:
    i. a signal shaping circuit (302), configured to generate a positive rectangular wave pulse signal upon receiving the microcontroller edge trigger, wherein the timing of a rising edge and a falling edge of the positive rectangular wave pulse signal are controlled by adjustable delay elements;
    ii. a buffer circuit (303), operatively connected to the signal shaping circuit (302), wherein the buffer circuit (303) is configured to convert the positive rectangular wave pulse signal of the signal shaping circuit (302) to a differential pulse,
  wherein when the microcontroller edge trigger is received, the signal shaping circuit (302) generates a positive rectangular wave pulse signal, wherein the positive rectangular wave pulse signal is sent to the buffer circuit (303), wherein the buffer circuit (303) transforms the positive rectangular wave pulse signal to the differential pulse, wherein the buffer circuit (303) applies the differential pulse signal to the LED (304);
  d. the LED (304), wherein the LED (304) is turned on when forward biased and turned off when reverse biased, wherein the LED is disposed such that the differential pulse of the buffer circuit (303) sweeps the LED (304) from a reverse biased voltage to a forward biased voltage resulting in a pulsing LED (304) having a pulse defined by the differential pulse;

e. the sampling chamber (104), in which a sample of a fluorescent material is disposed, wherein the LED (304) is disposed such that the light from the LED (304) illuminates the sample of fluorescent material;

f. a synchronization circuit (103) operatively connected to the signal shaping circuit (302) and the microcontroller edge trigger, such that the synchronization circuit (103) generates a second series of pulses, wherein the timing of the second series of pulses is controlled by adjustable delay elements, wherein the adjustable delay elements are configured such that the second series of pulses is synchronized to the pulse of the LED (304);

g. a photomultiplier tube gating and bias circuit ("PMT") (105) operatively connected to the synchronization circuit (103), wherein the second series of pulses gates the PMT (105) on, wherein a default state of the PMT (105) is off;

h. a transimpedance and voltage amplifier unit (106) operatively coupled to an anode of the PMT (105); and i. an analog to digital converter (ADC) (107) having a field-programmable gate array (FPGA) coupled to an output of the transimpedance and voltage amplifier unit (106);

wherein when the microcontroller edge trigger generates a pulse, the LED driver (300) converts the pulse to a differential pulse whereupon the pulse causes the LED (304) to emit light, whereupon the fluorescent material is excited and fluoresces, wherein the synchronization circuit (103) generates delayed signals which activate the PMT while the material is fluorescing, wherein the PMT (105) detects the fluorescence and sends the fluorescence as a data signal to the transimpedance and voltage amplifier unit (106), wherein amplification and filtering of the data signal is performed, wherein the data signal is sampled by the ADC (107).

In some embodiments, the second series of pulses synchronized to the pulse of the LED (304) gates the PMT (105) on immediately after the LED (304) turns off such that light entering the PMT (105) is a direct result of the fluorescence.

In some embodiments, the second series of pulses synchronized to the pulse of the LED (304) gates the PMT (105) such that a time when the PMT (105) is on overlaps with a time when the LED (304) is on, wherein the system further comprises an optical filter disposed on the PMT (105), wherein the optical filter has a wavelength which overlaps the wavelength of the LED but not the florescent material, such that light from the spectrum of the LED is filtered out of the light received by the PMT, while the florescence of the sample is not filtered.

In some embodiments, the signal shaping circuit (302) of the present system further comprises:

a. a first signal comparator (502), wherein the first signal comparator (502) generates a first step signal upon receiving the microcontroller edge trigger signal, wherein the first step signal steps from a zero voltage to a positive voltage;

b. a second signal comparator (503), connected to the output of the first signal comparator (502), wherein the second signal comparator (503) inverts the output of the first signal comparator (502), generating a second step signal which steps from a positive voltage to a zero voltage;

c. a first adjustable delay element (506), connected to the output of the first signal comparator (502), wherein the first adjustable delay element (506) delays the first step signal;

d. a second adjustable delay element (504), connected to the output of the second signal comparator (503), wherein the second adjustable delay element (504) delays the second step signal; and e. a logical NAND gate element (505), which performs a logical NAND operation on the delayed first step signal and the delayed second step signal, resulting in an inverted pulse signal, wherein the inverted pulse signal has a width precisely controlled by the first adjustable delay element (506) and the second adjustable delay element (504).

In some embodiments, the signal shaping circuit (302) of the present system further comprises a synchronization output (510), connected to the output of the first signal comparator (502) and the output of the second signal comparator (503), wherein the rising edge of a pulse provides additional synchronization signals.

In some embodiments, a third signal comparator (507) of the present system is connected to the output of the NAND gate element (505), which is configured to level shift the inverted pulse signal to a desired voltage level before sending the signal to the buffer circuit (303).

In some embodiments, the first and second signal comparators (502, 503) of the present system are powered by a positive power rail, wherein the power of the power rail is regulated by a low drop out linear voltage regulator, wherein noise on the power rails is reduced by a low pass filter.

In some embodiments, the adjustable delay elements (504, 506) of the present system comprise a coarse adjustable delay element and a fine adjustable delay element, wherein the coarse adjustable delay element comprises a large value resistor and a variable capacitor in a low pass filter configuration, wherein the fine adjustable delay element comprises a small value resistor and a variable capacitor in a low pass filter configuration (509), wherein each variable capacitor can be used to adjust a delay of the adjustable delay elements (504, 506).

In some embodiments, the fine adjustable delay element of the present system comprises a 500 Ohm resistor and a variable capacitor with a range of about 8 picoFarads to 45 picoFarads.

In some embodiments, the inverted pulse signal of the signal shaping circuit (302) of the present system sweeps with a rectangular pulse from −2.5V to +2.5V.

In some embodiments, the synchronization circuit (103) of the present system comprises:

a. a logical NOR gate operatively coupled to a first synchronization comparator via a first capacitor, wherein input to the NOR gate is the synchronization output (510) of the signal shaping circuit (302), wherein the first synchronization comparator is coupled to a first delay element to produce a first PMT gating signal;

b. a second synchronization comparator coupled to a second delay element, wherein an output of the second delay element is a second PMT gating signal; and c. a third delay element coupled to a third synchronization comparator, wherein an output of the third synchronization comparator triggers sampling of a final output of the synchronization circuit (103);

wherein the first synchronization comparator, the second synchronization comparator, and the third synchronization comparator operate to make the rising edge and the falling edge of the microcontroller edge trigger sharp (less than a nanosecond), wherein the first delay element, the second delay element, and the third delay element delays the pulse to a desired time.

In some embodiments, sampling of the data signal is performed by an oscilloscope.

In some embodiments, the buffer circuit (303) of the present system comprises:
a. a buffer comparator (406), configured to generate a positive version of an input pulse of the buffer circuit (303), wherein the input pulse is a pulse with minimum transmission line reflection received from the signal shaping circuit (302);
b. a buffer comparator (402), configured to generate a negative version of the input pulse;
c. a first inverter (403), connected to the first buffer comparator (406), which inverts the positive version of the input pulse; and
d. a second inverter (404), connected to the second buffer comparator (402), which inverts the negative version of the input pulse;
wherein a signal between the first and second inverter (403, 404) is a differential pulse, wherein the LED (409) is connected between the first and second inverter (403, 404), wherein the LED (409) is disposed such that the differential pulse first sweeps the LED (409) to a forward biased state, followed by a reverse biased state.

In some embodiments, the buffer circuit (303) of the present system further comprises:
a. a first plurality of inverters (403) connected in parallel to the first buffer comparator (406); and
b. a second plurality of inverters (404) connected in parallel to the second buffer comparator (402);
wherein the LED (409) is connected between the first plurality of inverters (403) and the second plurality of inverters (404), wherein each plurality of inverters (403, 404) are configured to switch at precisely the same time, wherein connecting each set of the plurality of inverters (403, 404) in parallel reduces the series (output) resistance of the buffer circuit (303).

In some embodiments, the first plurality of inverters (403) of the present system comprises about 16 inverters and the second plurality of inverters (404) comprises about 16 inverters, wherein a resistance of the driving circuit is about 4 Ohms.

In some embodiments, each plurality of inverters (403, 404) of the present system are implemented on a miniature logic chip to minimize the path of a current driving the LED (409).

In some embodiments, the first buffer comparator (406) and the second buffer comparator (402) of the present system are powered by positive and negative power rails, wherein a power of the positive and negative power rails is regulated by a low drop out linear voltage regulator, wherein noise on the positive and negative power rails is reduced by a low pass filter.

In some embodiments, the power supply decoupling capacitors of the present system are placed across positive and negative power pins of the power rails, wherein an effective current path through the LED (409) is reduced to travelling from one decoupling capacitor through one inverter (403), through the LED (409), through the other inverter (404), to the other decoupling capacitor, wherein the reduction in high frequency current path decreases the parasitic inductance of the circuit, wherein the decrease in parasitic inductance decreases the LED intensity fall time of the circuit.

In some embodiments, the buffer circuit of the present system further comprises:
a. a third buffer comparator (401), configured to receive a pulse using a terminated transmission line from the signal shaping circuit (302), before copying the pulse to the first and second buffer comparators (406, 402); and
b. a fourth buffer comparator (405), configured to copy the output of the first buffer comparator, to provide a terminated transmission line synchronization signal output.

In some embodiments, the ADC (107) sampling of the present system is triggered by signal synchronized with the pulse of the LED via the synchronization signal output obtained from the buffer circuit (303).

In some embodiments, the FPGA of the present system averages multiple decays of the sampled data signal to produce an averaged decay signal which is subsequently processed via the PC to ascertain if a measureable fluorescence occurred, wherein the PC (108) displays acquired data.

In some embodiments of the present system, a differential pulse output of the buffer circuit forward biases the LED by +5V and then reverse biases the LED by −5V.

In some embodiments of the present system, 90% to 10% fall time of the LED is less than or equal to 2.6 nanoseconds.

In some embodiments of the present system, the buffer circuit is implemented on a printed circuit board, wherein the printed circuit board of the buffer stage includes a ground plane to minimize the current path through the LED.

In some embodiments of the present system, the differential pulse width is configurable to less than 2 nanoseconds, wherein an inherent rise time of the LED is such that the LED is unable to reach a maximum power output within the differential pulse width, wherein an ability of the LED to reach the maximum power output increases as a power level decreases.

In some embodiments of the present system, a plurality of buffer circuits are implemented in parallel to drive a plurality LEDs (409), wherein a higher output intensity is achieved by combining the plurality of LEDs (409) driven at a reduced power.

In some embodiments of the present system, a single buffer circuit with a plurality of inverters may drive the plurality of LEDs (409) at the cost of slower LED dynamics.

BRIEF DESCRIPTION OF THE DRAWINGS

The features and advantages of the present invention will become apparent from a consideration of the following detailed description presented in connection with the accompanying drawings in which.

DESCRIPTION OF PREFERRED EMBODIMENTS

Figure 1:
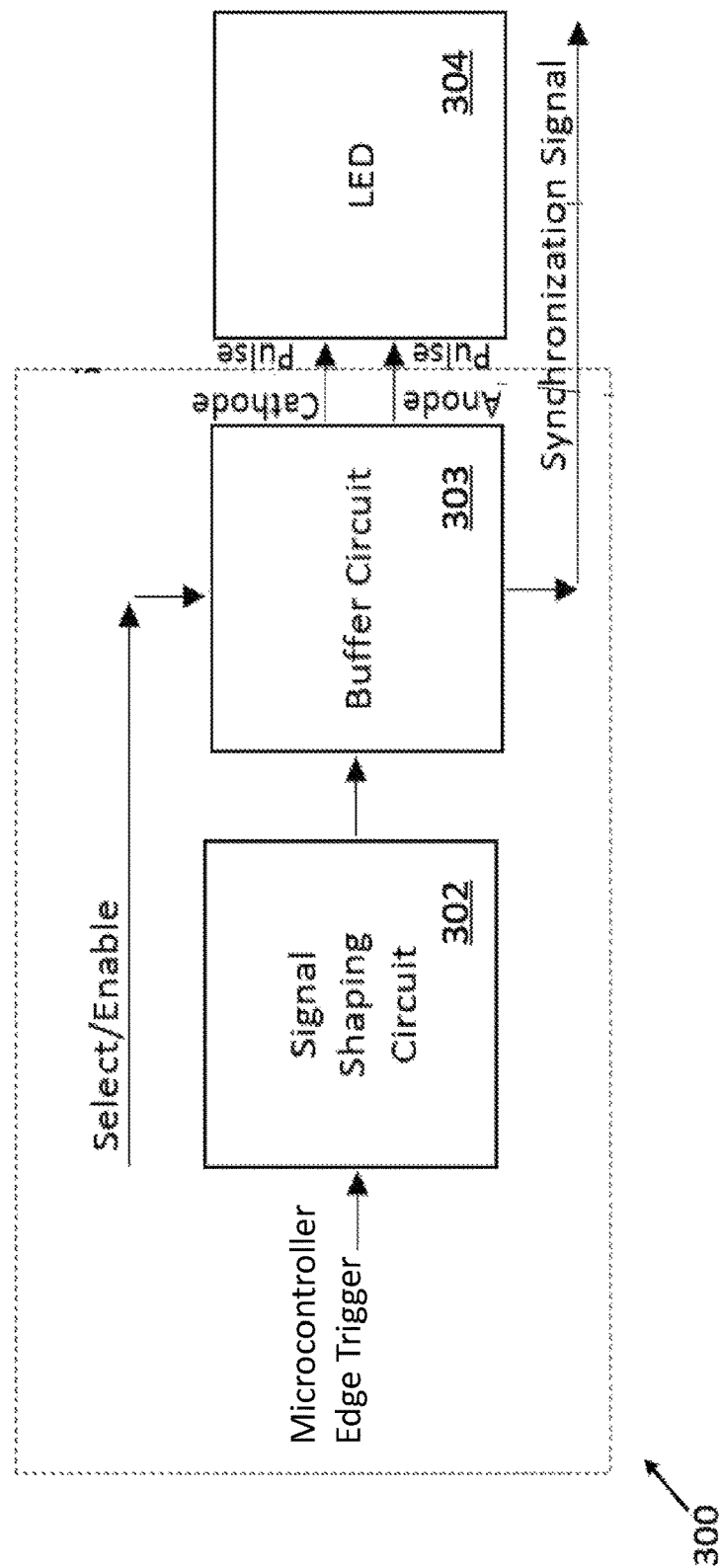
FIG. 1 shows a conceptual block diagram of the proposed LED pulsing driver circuit.
Figure 2:
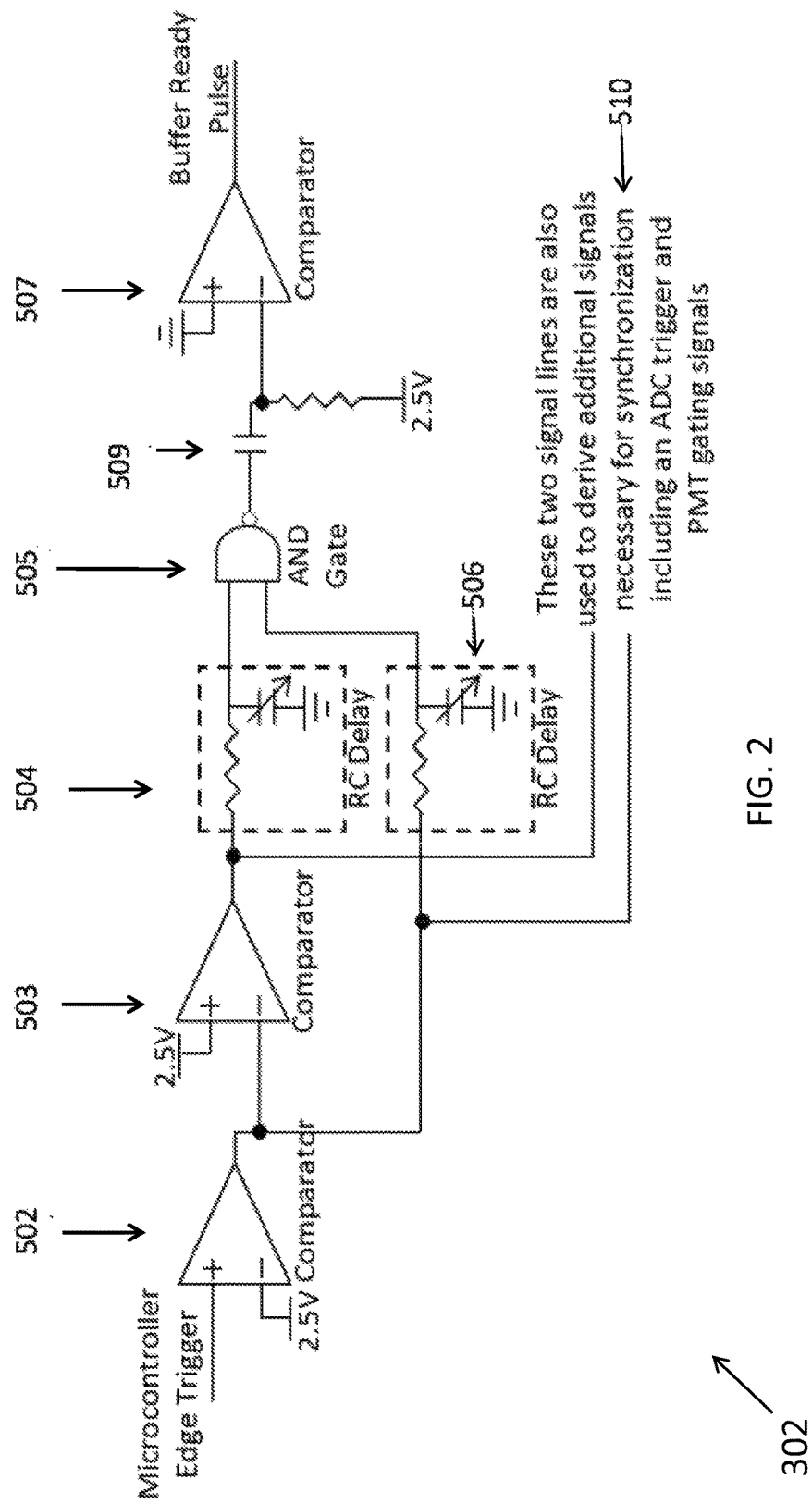
FIG. 2 shows a schematic of the signal shaping circuit of the time-resolved, transient recording fluorescence system of the present invention. Note that this is a subcircuit of FIG. 9.
Figure 3:
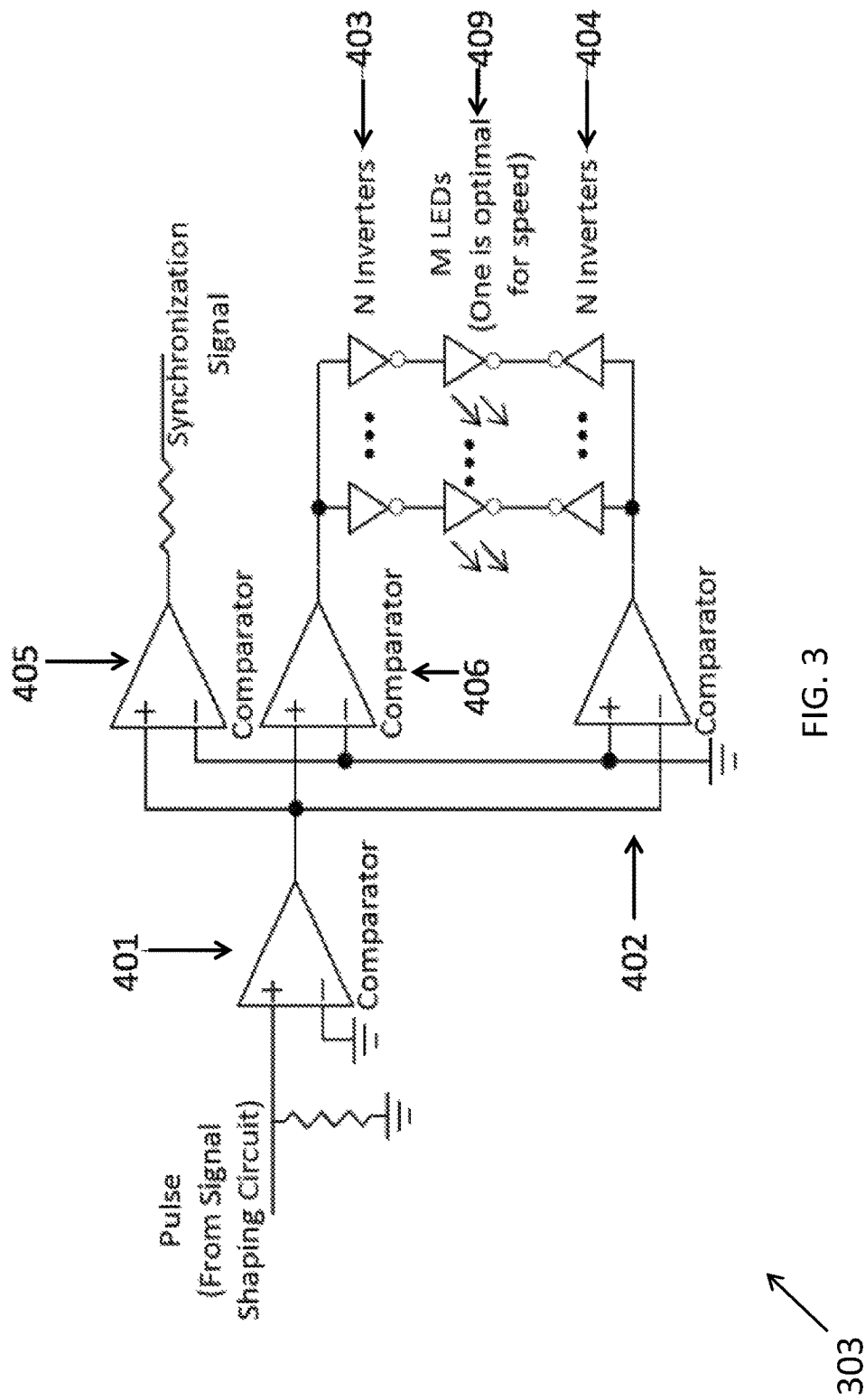
FIG. 3 shows a schematic of the buffer circuit of the present invention.

Referring now to FIGS. 1-3, the present invention features a high-intensity, ultra-short, light-emitting diode (LED) pulsing driver circuit (300), capable of driving an LED (304) with short duration, high-intensity pulses. In an embodiment of the present invention, the LED pulsing driver circuit (300) comprises a signal shaping circuit (302) and a buffer circuit (303). Upon receiving an edge trigger, the signal shaping circuit (302) may generate a positive rectangular wave pulse signal, where the timing of the rising and falling edges of the pulse may be controlled by adjustable delay elements. The buffer circuit (303), operatively connected to the signal shaping circuit, may convert the pulse signal of the signal shaping circuit (302) to a differential pulse. This differential pulse may sweep the LED (304) from a reverse biased to a forward biased voltage followed by a reverse biased voltage. The LED (304) is turned on when forward biased and turned off when reverse biased.

In a further embodiment, the signal shaping circuit (302) may comprise a first comparator (502) and a second comparator (503). The first comparator (502) may generate a first step signal upon receiving the edge trigger signal, where the first step signal may step from a zero voltage to a positive voltage. Inverting the output of the first comparator (502), the second comparator (503) may generate a second step signal which steps from a positive voltage back to zero voltage. In other embodiments, a first adjustable delay element (506), operatively connected to the output of the first comparator (502), and a second adjustable delay element (504) further comprise the signal shaping circuit (302). The first adjustable delay element (506) operates to delay the first step signal and the second adjustable delay element (504), operatively connected to the output of the second comparator (503), delays the second step signal. A logical NAND gate element (505) may also comprise the signal shaping circuit (302) of the LED pulsing driver circuit (300). This gate element (505) may perform a logical NAND operation of the delayed first step signal and the delayed second step signal, resulting in an inverted pulse signal. The width of this pulse signal is precisely controlled by the first adjustable delay element (506) and the second adjustable delay element (504). Another embodiment features a third comparator (507) connected to the output of the NAND gate element (505) and configured to level shift the inverted pulse signal to a desired voltage level before sending it to the buffer circuit (508). In some embodiments this level shifted inverter pulse signal sweeps with a rectangular pulse from −2.5V to +2.5V.

Another embodiment of the signal shaping circuit (302) of the LED pulsing driver circuit (300) features a synchronization output (510), connected to the output of the first comparator (502), wherein the rising edge of a pulse provides a synchronization signal.

In some embodiments, the first (502) and second (503) comparators are powered by a positive power rail, where the power of the power rail is regulated by a low drop out linear voltage regulator. Additionally, a low pass filter may be employed to reduce noise on the power rails.

In some embodiments, the adjustable delay elements (504, 506) of the present invention may further comprise coarse and fine adjustable delay elements. The coarse adjustable delay element may comprise a large value resistor and a variable capacitor in a low pass filter configuration. A small value resistor and a variable capacitor in a low pass filter configuration (509) may comprise the fine adjustable delay element, where each variable capacitor may be used to adjust a delay of the adjustable delay elements (504, 506). In some embodiments, the fine adjustable delay element comprises a 500 Ohm resistor and a variable capacitor with a range of about 8 picoFarads to 45 picoFarads. All variable and fixed resistors on the market and all variable and fixed capacitors on the market can be used for fine and course delay elements, however, fixed value thin film resistors and variable ceramic capacitors are preferred for their superior frequency response. The fine and course adjustable delay elements generate a minimum delay of about $t_{delay}=RC_{min}V_{ref}$ and a maximum delay of about $t_{delay}=RC_{max}Vref$ where R is the resistor value, $C_{min}$ and $C_{max}$ are the variable capacitor extreme values, and $V_{ref}$ is the voltage change required to cause the comparator to switch states located after the delay element. Any value for R, $C_{max}$, $C_{min}$, and $V_{ref}$ can be selected. For the prototype, course and fine delay elements were used with delays spanning about 560 ns to 100 ns and 56 ns to 10 ns for course and fine delay elements respectively. Resolutions in practice were about 1 ns and 200 ps for the prototype course and fine delay elements respectively.

In an embodiment of the present invention, the buffer circuit (303) may comprise a first comparator (406), a second comparator (402), a first inverter (403) connected to the first comparator (406), and a second inverter (404) connected to the second comparator (402). In some embodiments the first comparator (406) may be configured to generate a positive version of an input pulse of the buffer circuit (303), where the input pulse is the output of the signal shaping circuit (302) (e.g. the inverted pulse signal). Additionally, the second comparator (402) may be configured to generate a negative version of the input pulse. The first inverter (403) inverts the positive version of the input pulse while the second inverter (404) inverts the negative version of the input pulse. In some embodiments, a signal between the first and second inverter (403, 404) is a differential pulse, where the LED (409) is connected between the first and second inverter (403, 404). Further, the LED (409) may be disposed such that the differential pulse first sweeps the LED (409) to a forward biased state, followed by a reverse biased state.

In some embodiments of the present invention, the buffer circuit (303) may further comprise a first plurality of inverters (403) connected in parallel to the first comparator (406) and a second plurality of inverters (404) connected in parallel to the second comparator (402). Connecting each set of inverters (403, 404) in parallel reduces the series resistance of the buffer circuit (303). The LED (409) may be connected between the first plurality of inverters (403) and the second plurality of inverters (404). Each plurality of inverters (403, 404) may be configured to switch at precisely the same time.

Another embodiment of the buffer circuit (303) in the present invention features the first plurality of inverters (403) comprising 16 inverters and the second plurality of inverters (404) also comprising 16 inverters, where a resistance of the LED pulsing driver circuit (300) is about 4 Ohms. Further each plurality of inverters (403, 404) may be implemented on a miniature logic chip to minimize the path of a current driving the LED (409).

In some embodiments, the first comparator (406) and the second comparator (402) of the present invention may be powered by positive and negative power rails. A low drop out linear voltage regulator may regulate the power of the power rails and noise on the power rails may be reduced by utilizing a low pass filter. Power supply decoupling capacitors may be placed across the positive and negative power pins of the power rails, in this way the effective current path through the LED (304, 409) is reduced to travelling from one decoupling capacitor through one inverter (403), through the LED (304, 409), through the other inverter (404), to the other decoupling capacitor. This reduction in current path decreases the parasitic inductance of the circuit, effectively decreasing the LED (304, 409) intensity fall time of the circuit.

In some embodiments of the present invention, the buffer circuit (303) may further comprise a third comparator (401) and a fourth comparator (405). The third comparator (401) may be configured to receive a pulse with minimum transmission line reflection from the signal shaping circuit, before copying it to the first and second comparators. The fourth comparator (405), configured to copy the output of the first comparator, provides a terminated transmission line synchronization signal output. Further, the differential pulse output of the buffer circuit may forward bias the LED by +5V and then reverse bias the LED by −5V. The 90% to 10% fall time of the LED may be less than or equal to 2.6 nanoseconds. In some embodiments, the differential pulse width is configurable to less than 2 nanoseconds and the inherent rise time of the LED is such that the LED is unable to reach the maximum power output within the pulse width. The LED is more efficient at a reduced power level. The prototype sensor (PMT) and output circuitry was not able to measure the actual fall time of the LED due to having a limited bandwidth, but theoretical values were calculated on the order of 200 ps.

Additional embodiments of the present invention feature the buffer stage implemented on a printed circuit board, where the printed circuit board may include a ground plane to minimize the current path through the LED. Further, multiple buffer circuits may be implemented in parallel to drive multiple LEDs, where a higher output intensity is achieved by combining multiple LEDs driven at a reduced power. A single buffer circuit with a plurality of inverters may drive multiple LEDs at the cost of slower LED dynamics.

Referring now to FIGS. 4-14, the present invention further features a system employing the LED pulsing driver circuit (300) detailed earlier for effective time-resolved, transient recording of fluorescent lifetimes. In one embodiment, the system features a first personal computer (PC) graphical interface (101) initiating a series of pulses ("microcontroller edge trigger") from a microcontroller (102), where the microcontroller edge trigger may trigger the LED pulsing driver circuit (300) previously detailed. Further, the LED pulsing driver circuit (300) may be operatively coupled to a sampling board (104) upon which a sample of a fluorescent material is disposed.

In additional embodiments of the present invention, a synchronization circuit (103) may be operatively connected to the signal shaping circuit (302) of the LED pulsing driver circuit (300) such that the synchronization circuit (103) generates a second series of pulses synchronized to the pulse of the LED (304). Further, a photomultiplier tube gating and bias circuit ("PMT") (105) may be operatively connected to the synchronization circuit (103), where the second series of pulses synchronized to the pulse of the LED (304) gates the PMT (105) on (note: the default state of the PMT (105) is off). A transimpedance and voltage amplifier unit (106) operatively coupled to an anode of the PMT (105) may further comprise the system, where an analog to digital converter (ADC) with a field-programmable gate array (FPGA) may be coupled to its (106) output.

Consistent with previous embodiments of the present system, the fluorescent material is excited and fluoresces when the pulsing LED (304) is triggered on. The PMT (105) records the fluorescence and sends the fluorescence as a data signal to the transimpedance and voltage amplifier unit (106) where amplification and filtering of the data signal may be performed. The data signal may then be sampled by the ADC (107), where sampling is triggered by a second signal synchronized with the pulse of the LED (via a synchronization signal obtained from the buffer circuit (303)). Following, the FPGA (107) may operate to average multiple decays of the sampled data signal to produce an averaged decay signal. This signal is subsequently processed via the PC to ascertain if a measureable fluorescence occurred. Additionally, data acquired may be displayed by the PC (108).

In some embodiments of the present invention, the second series of pulses synchronized to the pulse of the LED (304) may gate the PMT (105) on immediately after the LED (304) turns off. In this way, light entering the PMT (105) is a direct result of the fluorescence. An alternative embodiment features the second series of pulses gating the PMT (105) such that a time when the PMT (105) is turning on overlaps with a time when the LED (304) is turning off. Light entering the PMT (105) in this way is also a direct result of the fluorescence at the proper point in time.

In a further embodiment, the synchronization circuit (103) of the present system may comprise a NOR gate operatively coupled to a first comparator via a first capacitor, where input to the NOR gate is the synchronization output (510) of the signal shaping circuit (302). The first comparator may be coupled to a first delay element to produce a first PMT gating signal. A second comparator may be coupled to a second delay element having a second PMT gating signal as an output. A third delay element coupled to a third comparator may also be featured, where the output of the third comparator may be used to trigger sampling of the data signal. In one embodiment, sampling is accomplished via the ADC (107). An alternate embodiment utilizes an oscilloscope for sampling. The first comparator, the second comparator, and the third comparator may operate to make the rising edge and the falling edge of the microcontroller edge trigger sharp (less than a nanosecond). The delay elements delay an incoming pulse to achieve a desired timing.

Time-Resolved Transient Recording Fluorescence—System Level Information

Figure 4:
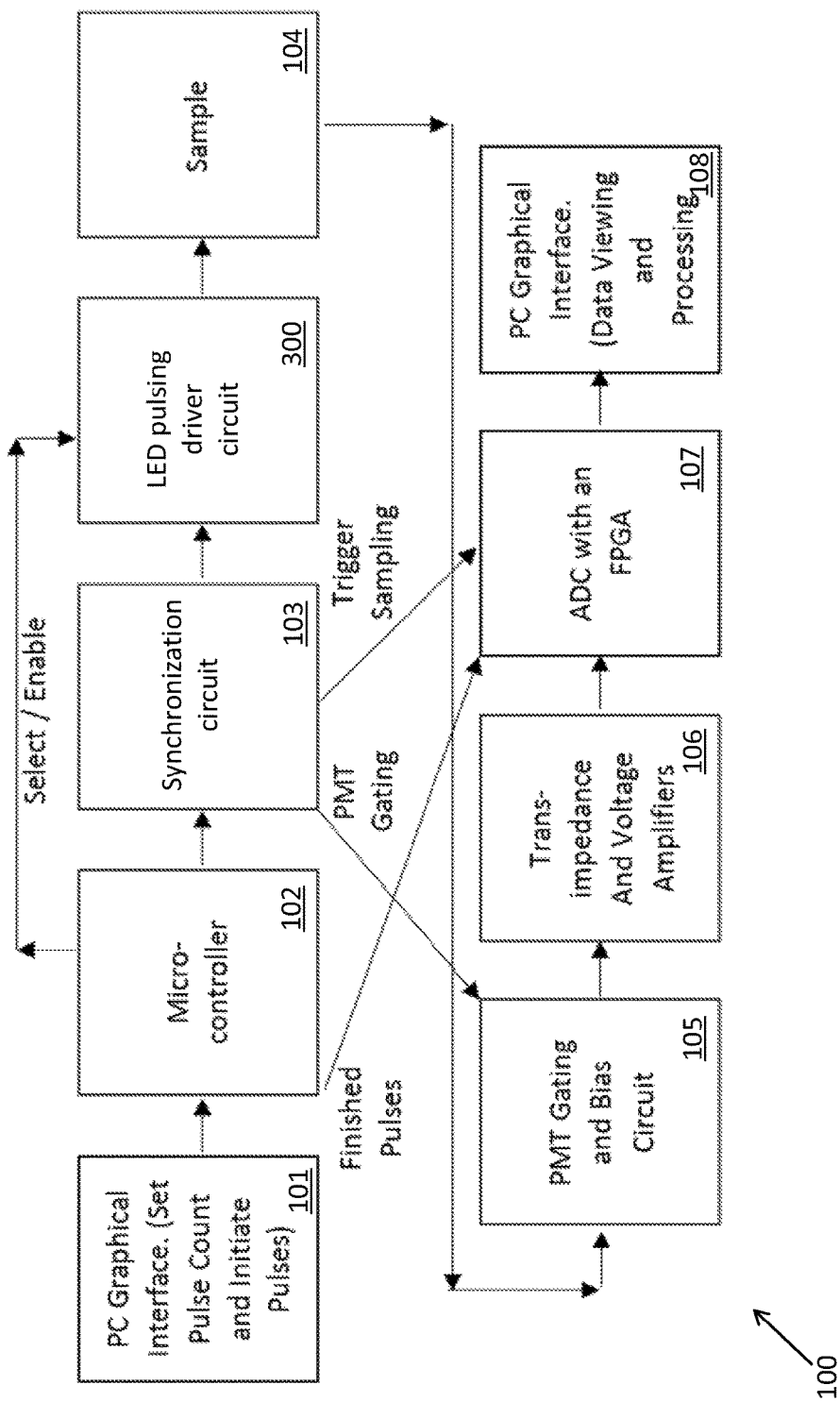
FIG. 4 shows a conceptual block diagram of an exemplary embodiment for the time-resolved, transient recording fluorescence system of the present invention.

In some embodiments of the present invention, a time-resolved fluorescence system capable of recording fluorescent lifetimes from fluorophores of about 2 ns or longer has been developed. FIG. 4 shows a diagram of the system. A PC initiates a series of pulses from a microcontroller. The microcontroller triggers a synchronization circuit to generate pulses to drive an LED depending on which LED is selected/enabled. Additionally, the synchronization circuit also generates pulses synchronized to the LED pulse to gate a PMT on and to initiate sampling. When the series of pulses is complete, the microcontroller signals to the sampling board to finish initial processing of the data (averaging) and to send the data to the PC. The fluorescent data is expected to have applications in cell quantification and identification. Furthermore, the electronic design is expected to be applicable in optical communications, general high speed instrumentation, and imaging. Additional applications of subcomponents will be subsequently discussed.

In some embodiments of the present system, an LED is pulsed to excite a sample which, in turn, fluoresces and the resulting fluorescence is recorded by a Photomultiplier Tube (PMT). The current signal from the PMT is amplified and filtered by a transimpedance amplifier and the resulting signal is sampled. The data is captured by an FPGA on-the-fly and multiple decays are averaged to minimize the amount of data as well as increase the signal-to-noise ratio (SNR). Finally, the averaged decay is processed by a Digital Signal Processor or a computer to ascertain if there is a measureable fluorescence.

Figure 5:
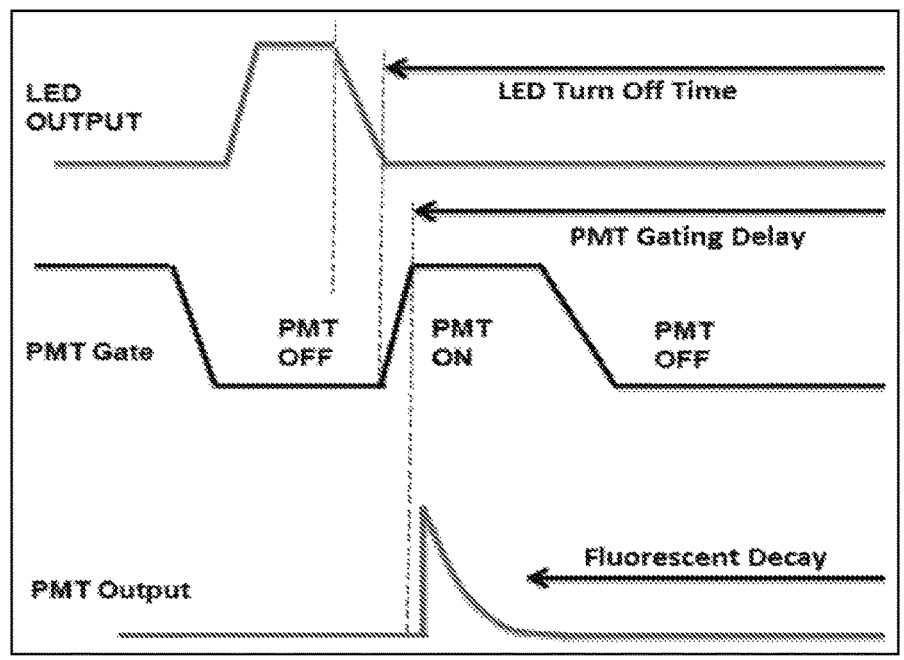
FIG. 5 shows a level timing diagram for the present invention.
Figure 6:
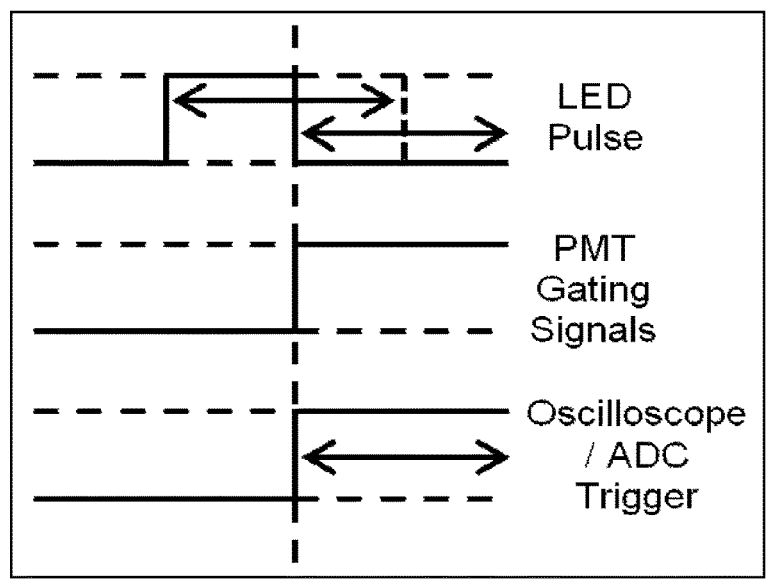
FIG. 6 shows an example of the relative timing of the synchronized pulses generated by the synchronization circuit. The arrows indicate that variable capacitors can be used to adjust the rising and falling edges times of the signals.

The timing diagram of FIG. 5 helps to further elucidate the operation of this system: an LED is pulsed, just after the LED turns off, the PMT begins turning on, and the only light that should be entering the PMT is the light from the fluorescing sample. In reality, the time during which the LED is turning off and the time that the PMT is turning on can be overlapped provided that the PMT's function and the function of the transimpedance and voltage amplification circuitry are not degraded by excessive excitation from the LED. The delay from the time that the LED begins to turn off to the time that the PMT output begins to respond can easily be measured, and a trigger edge can be set to begin sampling. This moment also corresponds to the beginning of the fluorescent decay.

High-Level System Description

Figure 7:
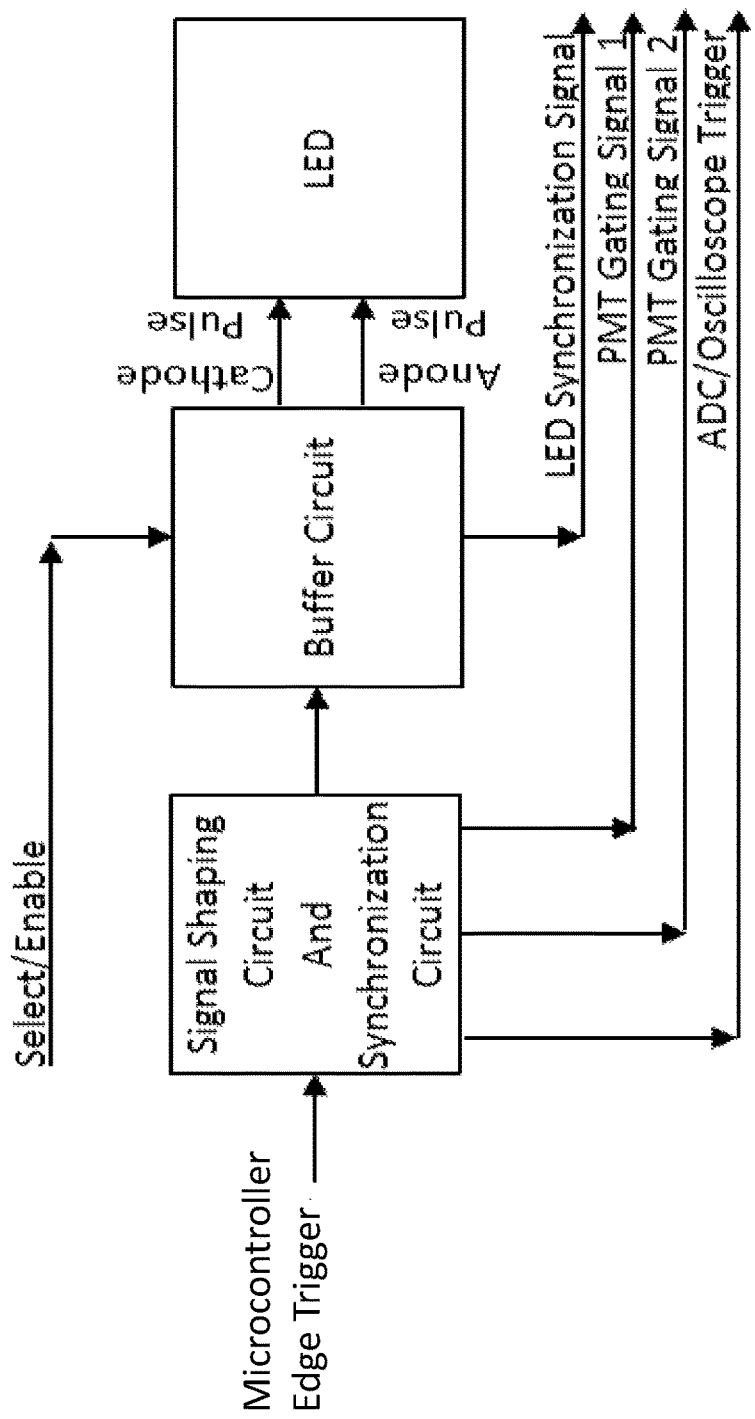
FIG. 7 shows a conceptual block diagram of an exemplary embodiment of the LED driver subsystem and synchronization system of the present invention.

FIG. 7 shows the LED Driver sub-system that is implemented in the conceptual system block diagram in FIG. 4 (in the Synchronization Circuit block and the LED pulsing driver circuit block). A trigger signal is generated by the microcontroller and by some discrete logic and analog comparators (synchronization circuit) in FIG. 4. The trigger signal is a rectangular pulse. The signal shaping circuit is used to change the pulse width of the trigger signal and to shift the voltage of the rectangular pulse to go from −2.5V to 2.5V instead of from 0V to 5V. The buffer circuit takes the new rectangular pulse and applies it to the LED. The buffer circuit provides the current necessary to drive the LED with the desired amount of power. It applies the signal differentially with an anode pulse and a cathode pulse to switch a greater amount of voltage across the LED. A synchronization signal is taken from the buffer signal in order to line up the LED pulse with another synchronization signal that starts the sampling from an Analog to Digital Converter (ADC).

Buffer Circuit Subsystem

A simplified version of the buffer circuit implementation for the LED Driver is shown in FIG. 3. The two resistors are 50 Ohms and account for transmission line effects. A perfectly synchronized negative and positive version of the pulse (together this makes a differential pulse) from the signal shaping circuit is generated by using comparators. The differential pulse is applied to an LED using inverters. In the actual circuit additional inverters are used to buffer the signals to the inverters driving the LEDs because 16 inverters are used on each side. Otherwise, the capacitance from the inverters slows down the switching speed of the comparators and unwanted timing jitter can be introduced. All chips are decoupled from the power rails with capacitors to prevent voltage droop during the pulse. All chips are powered with +/−2.5V.

Signal Shaping Circuit Subsystem

Figure 9:
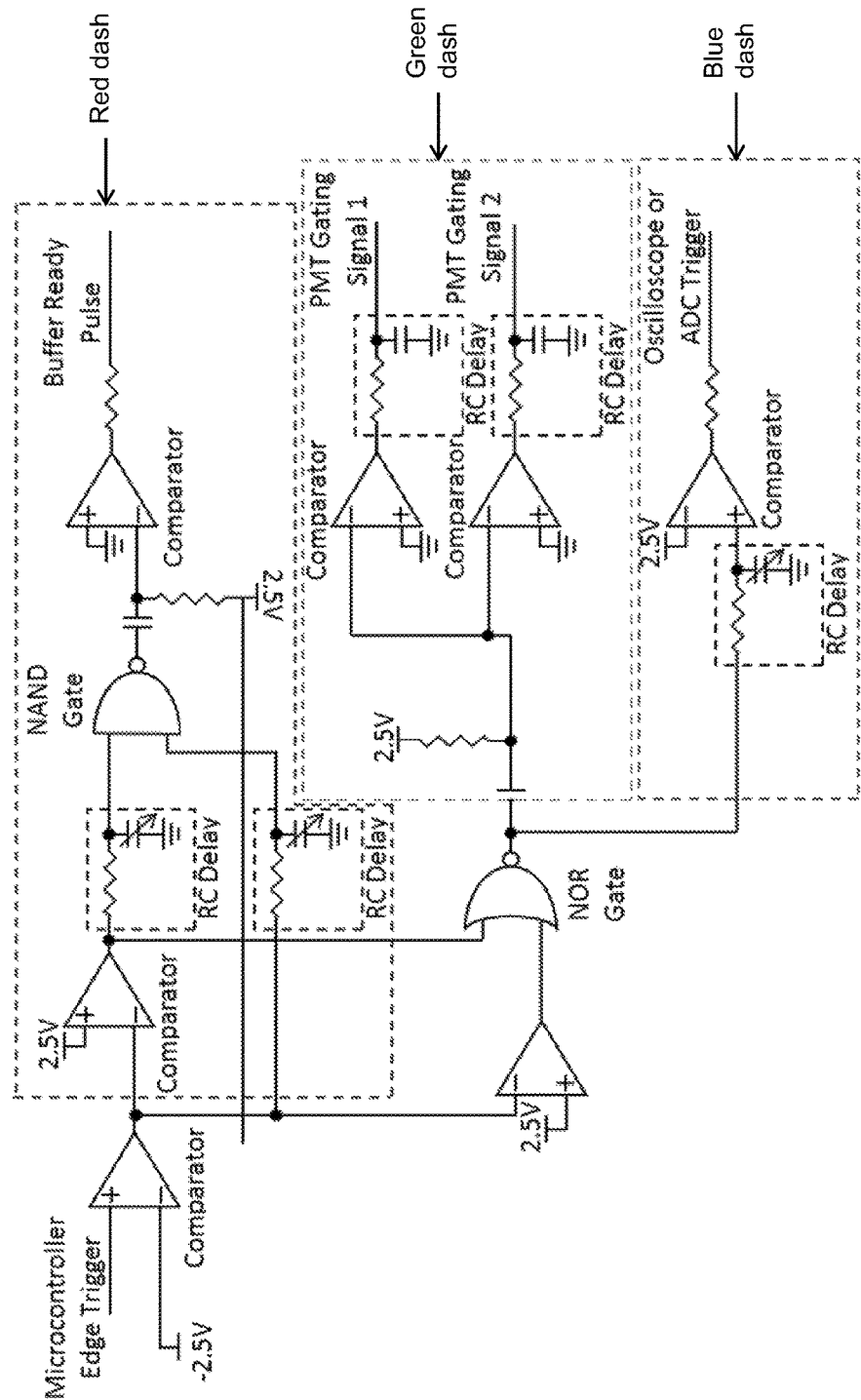
FIG. 9 shows a simplified diagram of the complete synchronization circuit of the present invention.

The signal shaping circuit of the LED driver is integrated into the Synchronization Circuit block as shown in FIG. 9. The isolated circuit is shown in FIG. 2. This uses far fewer components than would be necessary if each block was implemented independently. All synchronization circuit signals are derived from a single high-speed comparator that receives an edge trigger from a microcontroller. This minimizes jitter between all timing signals, including those used to gate the PMT sensor and to trigger the ADC. This circuit generates a pulse for an LED via the buffer circuit. The pulse can be varied in time by adjusting the variable capacitors in the circuit diagram. The last stage capacitively couples the resulting pulse to the final comparator in order to shift the voltage to the proper level before sending the signal to the LED buffer stage.

Synchronization Circuit Subsystem

FIG. 9 is a simplified circuit diagram of the complete synchronization circuit. Outlined in the dashed red line is the signal shaping part of the synchronization circuit used to drive an LED. In the actual circuit, there are four copies of the signal shaping circuit (except for the first two comparators) in parallel to drive multiple LEDs. Outlined in the dashed green line are circuits that generate two PMT gating signals, which are rectangular pulses close in duration to the pulse from the microcontroller. The original signal passes through a capacitor to set the proper voltage level of the pulse and the comparators make the rising and falling edges of the pulse sharp (less than a nanosecond). RC delay elements delay the pulses to position the PMT gating signals according to FIG. 6. Additionally, outlined in the dashed blue line, there is a branch of the circuit to trigger sampling of the final output of the signal by an oscilloscope or an ADC. The remaining components in the circuit produce the following effects: the first comparator generates a sharp (less than a nanosecond) transition from the slow edge of the microcontroller. The other comparator and NOR gate assist in producing the signal timing shown in FIG. 6.

PMT Biasing and Gating Subsystem

Figure 8:
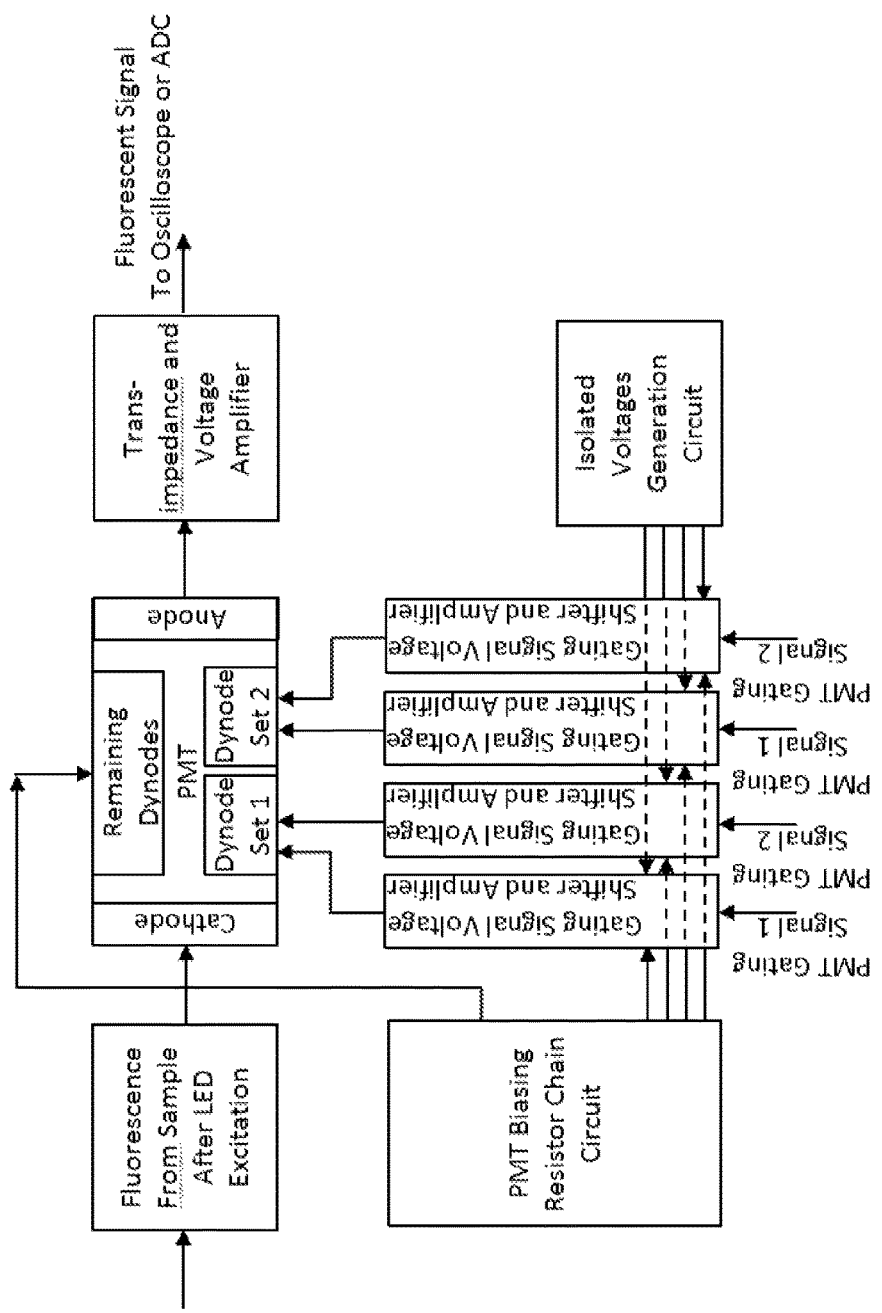
FIG. 8 shows an embodiment of the PMT gating and biasing subsystem coupled to the transimpedance and voltage amplifier circuit.

FIG. 8 is a diagram showing both the PMT Biasing and Gating Subsystem and the Transimpedance and Voltage Amplifier circuit block. Most of the dynode voltages are biased using the PMT Biasing Resistor Chain, which employs a high voltage regulator to generate voltages as low as −1000V. Additional voltages are generated in the resistor chain and used as reference voltages in the Gating Signal Voltage Shifter and Amplifier subcircuits. These references set the center voltage of the gating circuits. The gating circuits are powered by the Isolated Voltages Generation Circuit which sets the maximum possible voltages that can be produced by the outputs of the Gating Signal Voltage Shifter and Amplifier subcircuits.

PMT Biasing and Gating Subsystem—PMT Biasing Resistor Chain Circuit

Figure 10:
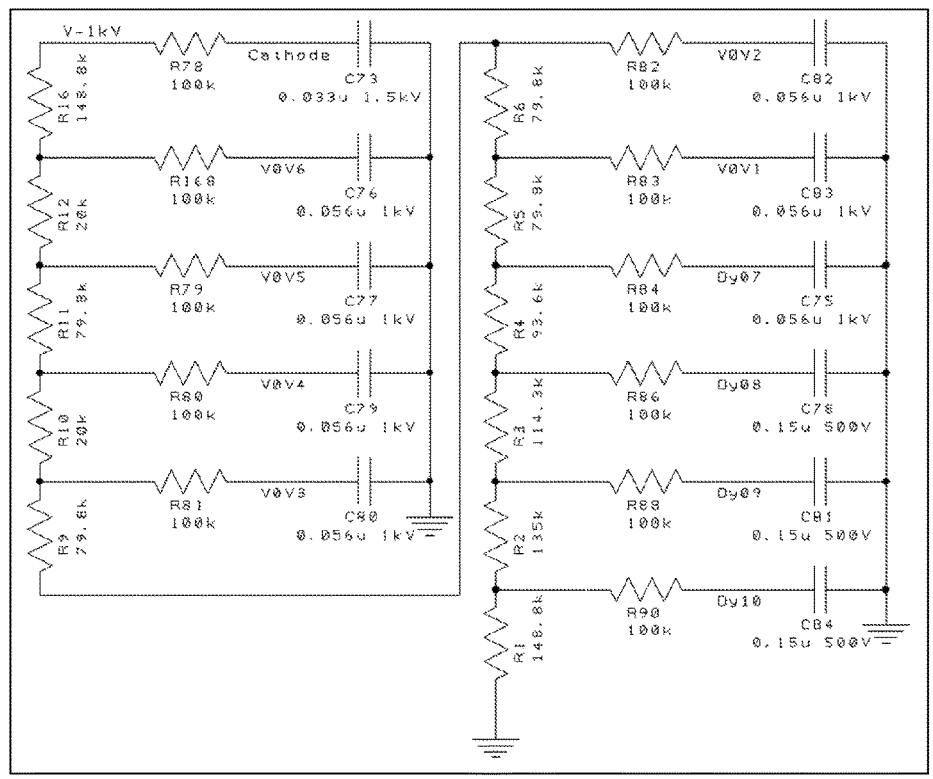
FIG. 10 is an illustration of an embodiment of the PMT biasing and resistor chain circuit.

FIG. 10 is a schematic of the PMT Biasing Resistor Chain Circuit. The node labeled V-1 kV has an implied connection to a −1 kV high voltage regulator. Table 1 below shows the names of nodes from FIG. 10 and the implied connections to other parts of the PMT Gating and Biasing Subsystem. The resistor and capacitor on each side of nodes Cathode, V0V6, V0V5, V0V4, V0V3, V0V2, V0V1, Dy07, Dy08, Dy09, and Dy10 form low pass filter circuits that perform two functions. First, they filter the noise from the switching regulator that generates the −1 kV voltage. Second, they are placed as close to the dynodes and gating circuits as possible to minimize spurious signals due to electromagnetic interference.

TABLE 1

Node Labeling of FIG. 10

| Node Name | Block From Sub-circuit Node is Connected to | Description |
| --- | --- | --- |
| Cathode | PMT | This node is connected to the cathode of the PMT |
| V0V6 | The Gating Signal Voltage Shifter and Amplifier Circuit for Dynode 1 | This node provides the center reference voltage for Gating Signal Voltage Shifter and Amplifier Circuit of Dynode 1 |
| V0V5 | The Gating Signal Voltage Shifter and Amplifier Circuit for Dynode 2 | This node provides the center reference voltage for Gating Signal Voltage Shifter and Amplifier Circuit of Dynode 2 |
| V0V4 | The Gating Signal Voltage Shifter and Amplifier Circuit for Dynode 3 | This node provides the center reference voltage for Gating Signal Voltage Shifter and Amplifier Circuit of Dynode 3 |
| V0V3 | The Gating Signal Voltage Shifter and Amplifier Circuit for Dynode 4 | This node provides the center reference voltage for Gating Signal Voltage Shifter and Amplifier Circuit of Dynode 4 |
| V0V2 | PMT | This node is connected to Dynode 5 of the PMT. Provision was made to generate more reference voltages if desired. |
| V0V1 | PMT | This node is connected to Dynode 6 of the PMT. Provision was made to generate more reference voltages if desired. |
| Dy07 | PMT | This node is connected to Dynode 7 of the PMT. |
| Dy08 | PMT | This node is connected to Dynode 8 of the PMT. |
| Dy09 | PMT | This node is connected to Dynode 9 of the PMT. |
| Dy10 | PMT | This node is connected to Dynode 10 of the PMT. |

PMT Biasing and Gating Subsystem—Gating Signal Voltage Shifter and Amplifier

Figure 11:
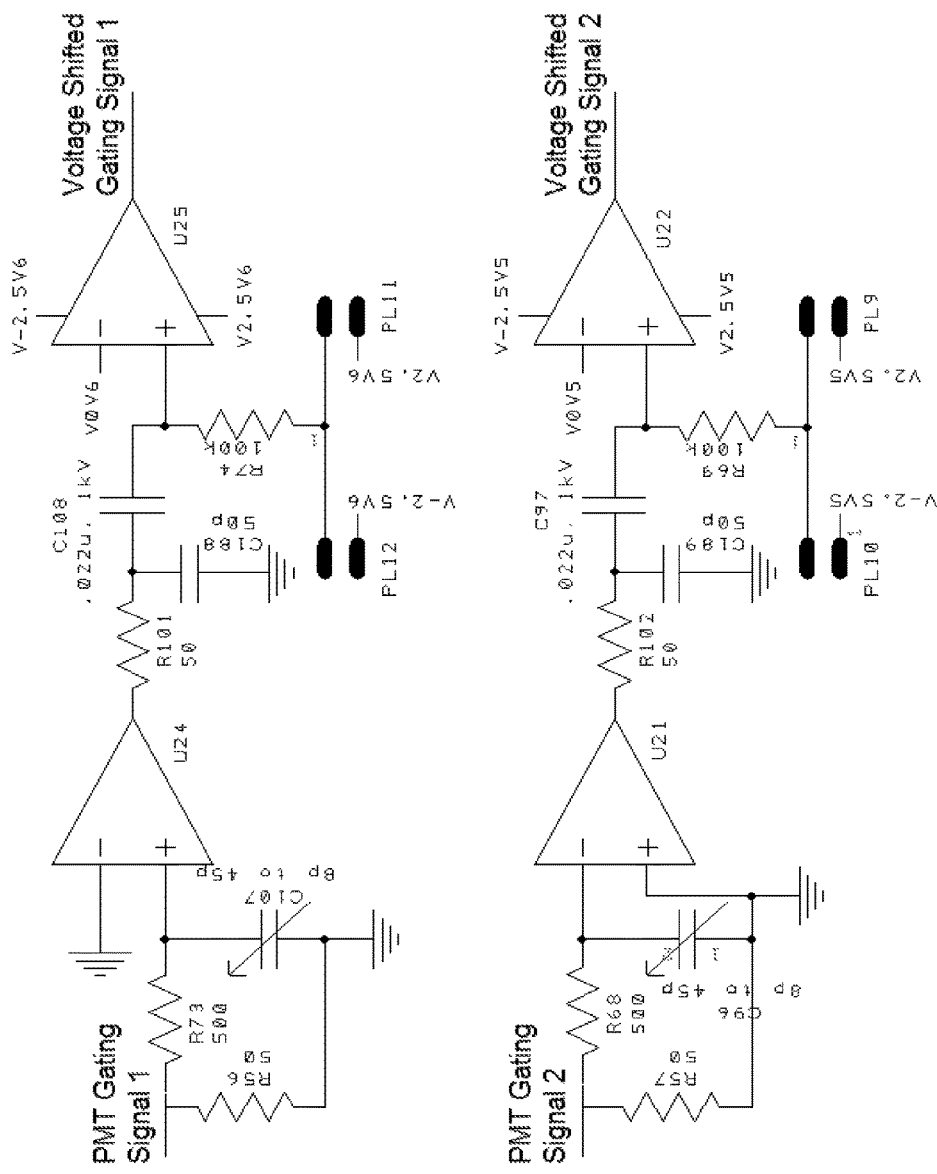
FIG. 11 is an illustration of an embodiment of the voltage shifter stage of two gating signal voltage shifter and amplifier circuits.

FIG. 11 shows the voltage shifter part of two Gating Signal Voltage Shifter and Amplifier circuits. Note that the nodes labeled V0V6 and V0V5 are the reference voltages generated by the PMT Biasing Resistor Chain Circuit. These circuits level shift two complimentary gating signals using capacitive coupling (C108 and C97). U24, U25, U21, and U22 are comparators. U21 and U24 eliminate any unintentional transmission line effects when the signals arrive from the Synchronization Circuit (FIG. 9). U21 inverts PMT Gating Signal 2 to have the opposite polarity as PMT Gating Signal 1. R73 and C107 form a delay element. R68 and C96 form another delay element. This allows the gating signals to be almost perfectly synchronized. R74 and R69 set the voltage of the noninverting inputs of U25 and U22 to +/−2.5V relative to V0V5 or V0V6 depending on the polarity of the gating signal. U25 and U22 also eliminate any ringing in the signal that can occur due to nonidealities (parasitic inductance, transmission line effects) due to C108 and C97. These capacitors have to be physically large due to voltage requirements and therefore exhibit more parasitic inductance than physically smaller capacitors with the same capacitance.

Figure 12:
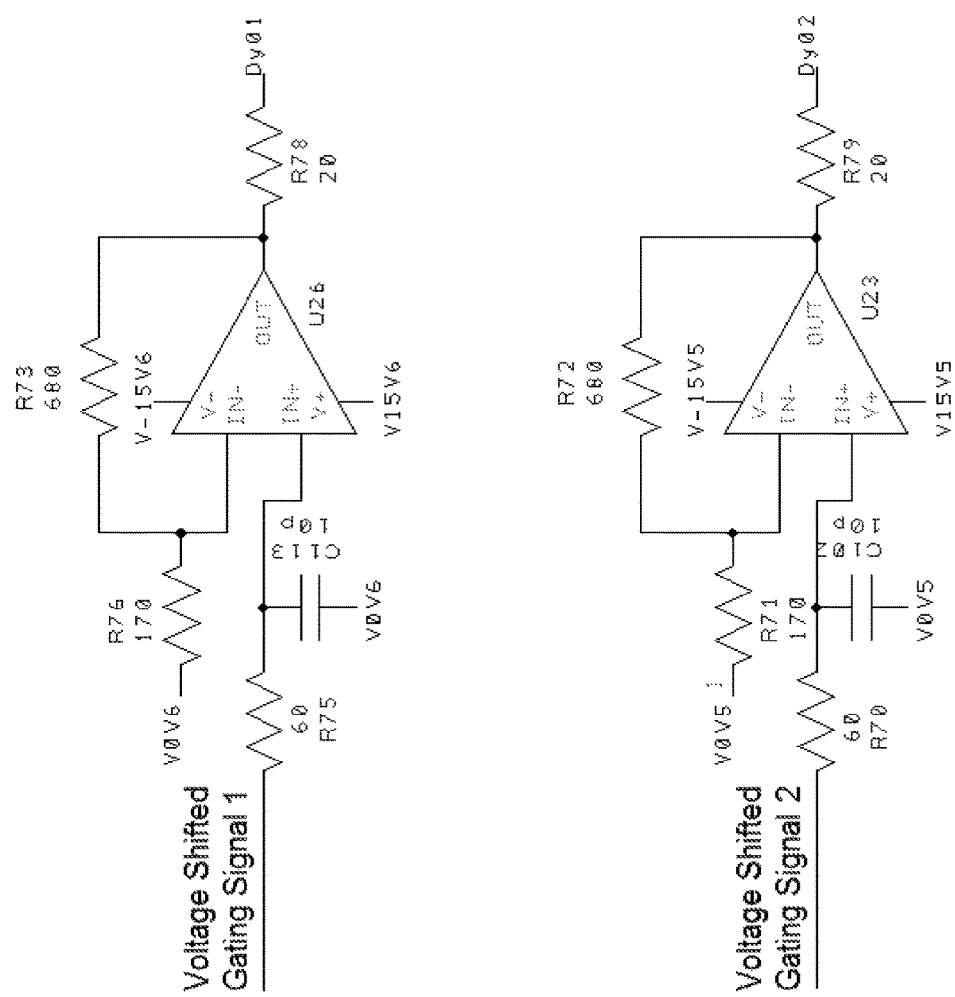
FIG. 12 is an illustration of the amplifier stage of two gating signal voltage shifter and amplifier circuits.

The output voltages, Voltage Shifted Gating Signals 1 and 2 then go to the inputs of the amplifier stages in FIG. 12. U23 and U26 are high voltage current feedback operational amplifiers. R75 together with C113 and R70 together with C102 form low pass filters. They reduce the high frequency content of the sharp edges from the comparators in the pervious stage. U23 and U26 have some peaking in the frequency response. The low pass filters reduce the ringing due to the peaking in the frequency response of U23 and U26.

PMT Biasing and Gating Subsystem—Isolated Voltages Generation Circuit

Figure 13:
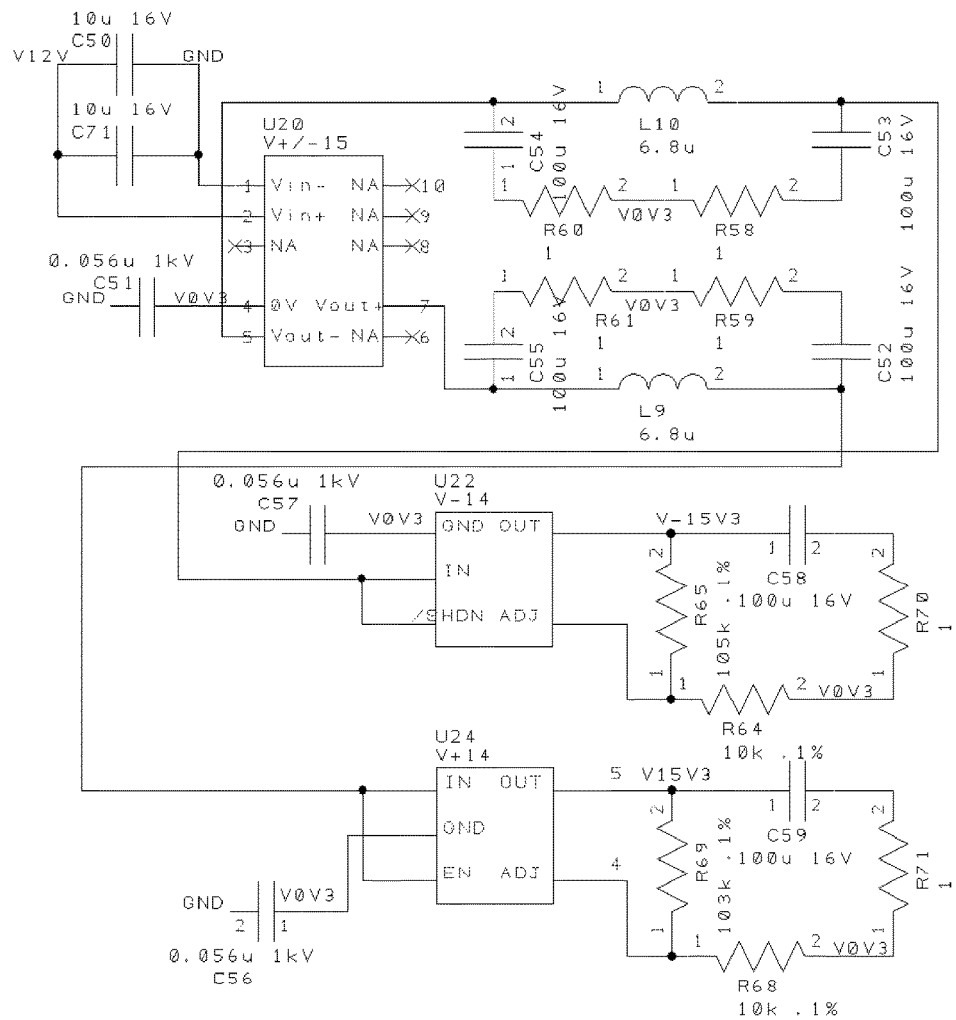
FIG. 13 illustrates one branch of the isolated voltages generation circuit.

FIG. 13 shows one of four identical circuits used to generate isolated power for each of the operational amplifiers in the Gating Signal Voltage Shifter and Amplifier circuits. Very similar circuits were used to power the comparators right before the operational amplifiers. These circuits produce isolated power with very little noise. The power must be isolated so that the reference voltage of these circuits can be shifted to be the center voltage about which a dynode on the PMT can be gated. For example, if the center voltage of one dynode is −600V, these circuits will produce two voltages, one at −585V and one at −615V. The operational amplifier will then output one of two voltages to the actual dynode to produce a 25V shift on a single dynode: one at −587.5V and one at −612.5V. The power is isolated up to 3 kV according to the datasheet. This rating only implies that the regulator can briefly handle 3 kV stresses for very brief periods of time. This is why 3 kV of isolation was chosen instead of 1 kV.

U20 is the switching, isolated regulator. RLC (Resistor, Inductor, and Capacitor) filters were used to filter the voltage generated by U20. U22 and U24 are Low Drop Out (LDO) regulators which have very good noise characteristics up to about 100 kHz. The final capacitor helps to stabilize the LDO regulator. V0V3 is the reference voltage that is tied into the Gating Signal Voltage Shifter and Amplifier and PMT Biasing Resistor Chain circuit.

PMT Biasing and Gating Subsystem—Transimpedance and Voltage Amplifier Circuit

Figure 14:
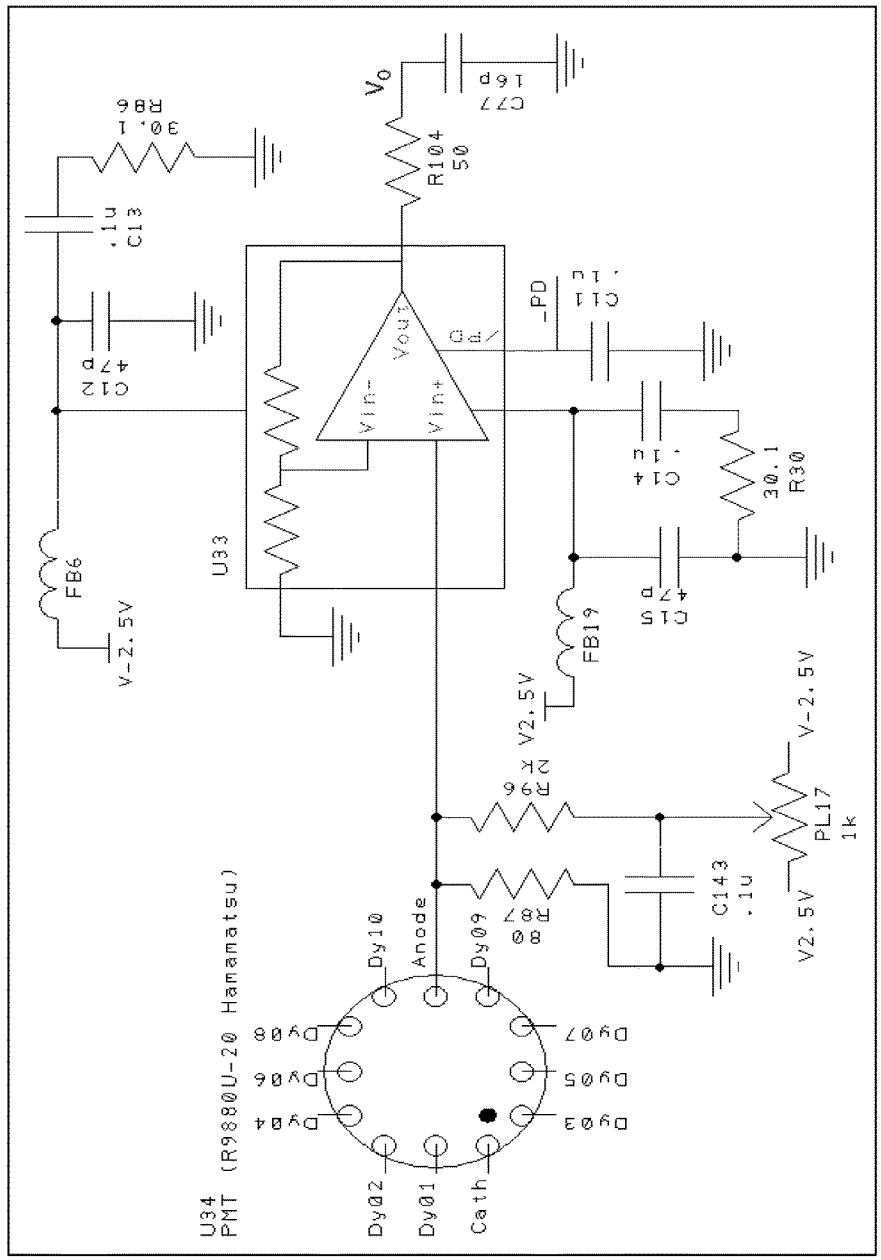
FIG. 14 is an illustration of the PMT connections and transimpedance and voltage amplifier circuit.

The circuit in FIG. 14 shows PMT connections and output to the Transimpedance and Voltage Amplifier circuit. R87 serves as the transimpedance amplifier. A single resistor was chosen to maximize bandwidth at the expense of noise. The potentiometer circuit comprising of R96 and PL17 allow the output voltage signal of the circuit to be shifted so that a wider range of the linear range of the operational amplifier can be used. The filter networks (FB6, C12, C13, R86 and FB19, C15, R30, C14) were chosen to allow the operational amplifier to operate as designed with a 1.8 GHz bandwidth and a gain of 10.

Functional Abilities of the Time-Resolved Transient Recording Fluorescence System In some embodiment of the present invention, the PMT biasing circuitry, gating circuitry, and transimpedance amplifier circuitry were designed to optimize the following features:

(1) Pulse linearity of 5% or better depending on the signal intensity (based on FIG. 4-47 Photomultiplier Tubes Basics and Applications $3^{rd}$ Edition by Hamamatsu) for voltage outputs as high as 0.7V.
(2) Minimize gain variation due to noise (less than 0.025% of the total gain).
(3) SNR approximately 2 for signals with intensities requiring a gain of $10^7$ to produce 250 mV signals. Minimized the total noise (measured to be about 125 mVpp at a PMT gain of about $10^7$). The DC signal was about 250 mV yielding an SNR of about 2.
(4) Minimize measurable lifetimes of exponential decays (estimated capability—approximately 1.6 ns, successfully measured a 2 ns lifetime of 23 µM of Acridine Orange in Single Stranded Nucleic Acid)
(5) Minimal gating transients of 20 mVpp with a gain of about $10^6$.
(6) Minimum gating turn on times
  (a) approximately 3.6 ns for one pair of dynodes, or
  (b) approximately 7.2 ns for two pairs of dynodes.

In some embodiments of the present invention, the LED Driver Subsystem together with the PMT Biasing and Gating Subsystem generate highly synchronized signals. All signals of interest are synchronized to much less than 200 ps with only about 200 ps of random jitter.
  (a) The LED pulse
  (b) The resulting fluorescent signal from the PMT and transimpedance amplifier circuitry
  (c) The PMT gating signals
  (d) The ADC trigger signal In some embodiments, by developing this gating and biasing circuitry for dynode chain PMTs, we can consistently record optical signals with intensities that change rapidly and can be defined such that the signals can have 10% to 90% rise times and with 90% to 10% fall times on the order of 1.75 ns and longer. Other technologies of this capability such as Microchannel Plate PMTs and Hybrid PMTs are at least 5 to 10 times more expensive. Additionally, the overall gain of the system is about $10^7$. Together with the high intensity, short duration synchronized LED light pulses, fluorescent decay data of fluorophores with concentrations lower than 100 nM can be recorded for some fluorophores depending on the quantum yield of the dye and the environment of the solution. Additionally, The gating circuitry allows observation of fluorescent signals resulting from high intensity LED pulses without light scatter from the LED pulses (driving the PMT and transimpedance amplifier circuitry to operate in a nonlinear region of operation). This is particularly advantageous when lower intensity LED pulses are not adequate to generate a strong enough signal to be detected by the PMT.

Pulse Linearity of 5% or Better

The dynodes were biased using a tapered voltage-divider scheme for the anode and last few dynodes, meaning the voltage was gradually increased (in general). In Photomultiplier Tubes and Assemblies For Scintillation Counting & High Energy Physics, Hamamatsu recommends various tapered-voltage-divider schemes depending on the number of dynodes for photomultiplier tubes. A voltage divider scheme was selected and slightly modified so as to still allow the dynodes to be gated with operational amplifiers. If the voltage gradient is too great between all the dynodes, then the PMT cannot be gated off using operational amplifiers.

Gain Variation of Less than 0.025% of the Total Gain Due to Voltage Regulator Switching Noise Resistor-Capacitor Filters were used from the voltage divider nodes to the dynodes to filter the noise from the switching regulators. The worst case is the cathode because there is the least resistance from the cathode to the voltage regulator. By estimating the gain variation from the cathode to the first dynode, assuming equal gain for all stages (an overestimate of the overall gain) and then multiplying by 10 (the number of gain stages) an overestimate of the gain variation can be calculated.

SNR of about 2 for Signals with Intensities Requiring a Gain of $10^7$ to Produce 250 mV Signals To achieve the highest gain using a photomultiplier tube, a dynode chain PMT was selected. All other types have lower gain. To get equivalent gain from electronic amplification introduces additional noise. Additionally, the gain variation was minimized.

Measurable Lifetimes of about 2 ns and Longer Depending on the Concentration and Quantum Efficiency of a Fluorophore.

A PMT was selected with a rise time of 0.57 ns. The cathode to first dynode voltage gradient was increased to reduce transit time spread which reduces the fall time of the PMT and allows to PMT to track faster exponential decays. It is estimated that the fall time is typically three to four times that of the rise time according to Hamamatsu. Since an exponential decay with a lifetime of about 2 ns was measured, which is a signal with a duration of 10 ns, fall times closer to only three times the rise time were likely achieved.

Minimal Gating Transients of 20 mV

The gating transients were reduced by using operational amplifiers to gate the dynodes. This minimizes voltage ringing on the dynodes due to the low output impedance of the operational amplifiers. Additionally, capacitors were used to reduce voltage variation on the dynodes to far less than 0.1%. Small capacitors were used in a "power supply decoupling configuration" (frequently found in digital circuits) close to the final dynodes to reduce the parasitic inductance which allow more rapid changes in current with even less change in the voltage.

Minimum Gating Turn on Times

High voltage current feedback operational amplifiers were types of operational amplifiers selected to gate the PMT on and off. The operational amplifiers could switch 25V with a 10% to 90% rise time or fall time of only about 3.5 ns.

Synchronization to within 200 ps

Synchronization was accomplished using two techniques primarily. The first technique is to derive all high speed signals from a single high speed comparator. The second is to minimize power supply noise using low drop out voltage regulators and filter circuits. Additionally, transmission line techniques (50 Ohm transmission cables and line termination) were used to reduce signal ringing and couple EMI emission back into the circuit.

Achieving Functional Abilities

The PMT Biasing circuitry was implemented to optimize the following features:
  (1) Maximum linearity
    a. Based Hamamatsu's PMT Handbook (2003) pulse linearity should be better than 5% for the linear range of the instrument based on FIG. 4-47.
    b. Selected a biasing scheme from Hamamatsu as follows
      i. Minimize space charge effects—gradually increased the voltage of the final dynodes in the dynode chain
      ii. Minimize transit time spread of the electrons—increased voltage gradient from the cathode to the first dynode
  (2) Minimize switching noise effects from the high voltage regulator used to generate the voltages for the dynode chain. This noise causes the gain of the PMT to fluctuate.
    a. Used a resistor chain to generate biasing voltages
    b. Used RC filter circuits to each dynode to filter switching noise
    c. Overestimated the maximum peak-to-peak ripple noise expected by using the highest cutoff frequency generated by the biasing circuit and RC circuits by using the circuit from the Cathode
      i. This yields a voltage gain variation of about 0.025% of the entire gain as opposed to 2.5% without the RC filters
  (3) Minimize EMI pickup on the signal traces by placing the above mentioned RC filters as close to the dynodes as possible.
  (4) Results from (2) and (3) peak-to-peak noise ripple across the spectrum can be estimated for the plots at about 125 mVpp at maximum PMT gain.

The PMT Gating circuitry was implemented to optimize the following features:
  (1) Operational amplifier based gating and capacitor decoupling to reduce effects of voltage droop at the dynodes due to sourcing charge.
    a. Results
      i. Minimum gating transients—About 20 mVpp with a gain of about $10^6$
      ii. Low nanosecond 10% to 90% turn-on time—about 3.6 ns
  (2) Successfully record data for lifetimes as short as 2 ns for high concentrations (e.g. 23 µM of Acridine Orange in Single Stranded Nucleic Acid).

As used herein, the term "about" refers to plus or minus 10% of the referenced number.

Various modifications of the present invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

REFERENCES

1. Photomultiplier Tubes: Basics and Applications, 3rd ed. Hamamatsu Co., Hamamatsu, Japan, 2006.
2. Hamamatsu, "Photomultiplier tube R9880U series," R9880U datasheet, 2010.
3. Photomultiplier Tubes and Assemblies For Scintillation Counting & High Energy Physics, Hamamatsu Co., Hamamatsu, Japan, 2012.

What is claimed is:

1. A system effective for time-resolved, transient recording of fluorescent lifetimes, the system comprising:
  a. a personal computer (PC) graphical interface (101), operatively coupled to a microcontroller, wherein the PC (101) initiates a series of pulses from the microcontroller (102), the PC (101) and microcontroller (102) collectively referred to as a microcontroller edge trigger;
  b. the microcontroller (102);
  c. a light emitting diode (LED) pulsing driver circuit (300), operatively connected to an LED (304), triggered by the microcontroller edge trigger, the LED pulsing driver circuit comprising:
    i. a signal shaping circuit (302), configured to generate a positive rectangular wave pulse signal upon receiving the microcontroller edge trigger, wherein the timing of a rising edge and a falling edge of the positive rectangular wave pulse signal are controlled by adjustable delay elements;
    ii. a buffer circuit (303), operatively connected to the signal shaping circuit (302), wherein the buffer circuit (303) is configured to convert the positive rectangular wave pulse signal of the signal shaping circuit (302) to a differential pulse,
  wherein when the microcontroller edge trigger is received, the signal shaping circuit (302) generates a positive rectangular wave pulse signal, wherein the positive rectangular wave pulse signal is sent to the buffer circuit (303), wherein the buffer circuit (303) transforms the positive rectangular wave pulse signal to the differential pulse, wherein the buffer circuit (303) applies the differential pulse signal to the LED (304);
  d. the LED (304), wherein the LED (304) is turned on when forward biased and turned off when reverse biased, wherein the LED is disposed such that the differential pulse of the buffer circuit (303) sweeps the LED (304) from a reverse biased voltage to a forward biased voltage resulting in a pulsing LED (304) having a pulse defined by the differential pulse;

e. a sampling chamber (104), in which a sample of a fluorescent material is disposed, wherein the LED (304) is disposed such that the light from the LED (304) illuminates the sample of fluorescent material;

f. a synchronization circuit (103) operatively connected to the signal shaping circuit (302) and the microcontroller edge trigger, such that the synchronization circuit (103) generates a second series of pulses, wherein the timing of the second series of pulses is controlled by adjustable delay elements, wherein the adjustable delay elements are configured such that the second series of pulses is synchronized to the pulse of the LED (304);

g. a photomultiplier tube gating and bias circuit ("PMT") (105) operatively connected to the synchronization circuit (103), wherein the second series of pulses gates the PMT (105) on, wherein a default state of the PMT (105) is off;

h. a transimpedance and voltage amplifier unit (106) operatively coupled to an anode of the PMT (105); and i. an analog to digital converter (ADC) (107) having a field-programmable gate array (FPGA) coupled to an output of the transimpedance and voltage amplifier unit (106);

wherein when the microcontroller edge trigger generates a pulse, the LED driver (300) converts the pulse to a differential pulse whereupon the pulse causes the LED (304) to emit light, whereupon the fluorescent material is excited and fluoresces, wherein the synchronization circuit (103) generates delayed signals which activate the PMT while the material is fluorescing, wherein the PMT (105) detects the fluorescence and sends the fluorescence as a data signal to the transimpedance and voltage amplifier unit (106), wherein amplification and filtering of the data signal is performed, wherein the data signal is sampled by the ADC (107).

2. The system of claim 1, wherein the second series of pulses synchronized to the pulse of the LED (304) gates the PMT (105) on immediately after the LED (304) turns off such that light entering the PMT (105) is a direct result of the fluorescence.

3. The system of claim 1, wherein the second series of pulses synchronized to the pulse of the LED (304) gates the PMT (105) such that a time when the PMT (105) is on overlaps with a time when the LED (304) is on, wherein the system further comprises an optical filter disposed on the PMT (105), wherein the optical filter has a wavelength which overlaps the wavelength of the LED but not the florescent material, such that light from the spectrum of the LED is filtered out of the light received by the PMT, while the florescence of the sample is not filtered.

4. The system of claim 1, wherein the signal shaping circuit (302) comprises:

a. a first signal comparator (502), wherein the first signal comparator (502) generates a first step signal upon receiving the microcontroller edge trigger signal, wherein the first step signal steps from a zero voltage to a positive voltage;

b. a second signal comparator (503), connected to the output of the first signal comparator (502), wherein the second signal comparator (503) inverts the output of the first signal comparator (502), generating a second step signal which steps from a positive voltage to a zero voltage;

c. a first adjustable delay element (506), connected to the output of the first signal comparator (502), wherein the first adjustable delay element (506) delays the first step signal;

d. a second adjustable delay element (504), connected to the output of the second signal comparator (503), wherein the second adjustable delay element (504) delays the second step signal; and e. a logical NAND gate element (505), which performs a logical NAND operation on the delayed first step signal and the delayed second step signal, resulting in an inverted pulse signal, wherein the inverted pulse signal has a width precisely controlled by the first adjustable delay element (506) and the second adjustable delay element (504).

5. The system of claim 4, wherein the signal shaping circuit (302) further comprises a synchronization output (510), connected to the output of the first signal comparator (502) and the output of the second signal comparator (503), wherein the rising edge of a pulse provides additional synchronization signals.

6. The system of claim 5, wherein the synchronization circuit (103) comprises:

a. a NOR gate operatively coupled to a first synchronization comparator via a first capacitor, wherein input to the NOR gate is the synchronization output (510) of the signal shaping circuit (302), wherein the first synchronization comparator is coupled to a first delay element to produce a first PMT gating signal;

b. a second synchronization comparator coupled to a second delay element, wherein an output of the second delay element is a second PMT gating signal; and c. a third delay element coupled to a third synchronization comparator, wherein an output of the third synchronization comparator triggers sampling of a final output of the synchronization circuit (103);

wherein the first synchronization comparator, the second synchronization comparator, and the third synchronization comparator operate to make the rising edge and the falling edge of the microcontroller edge trigger sharp (less than a nanosecond), wherein the first delay element, the second delay element, and the third delay element delays the pulse to a desired time.

7. The system of claim 6, wherein sampling of the data signal is performed by an oscilloscope.

8. The system of claim 4, wherein a third signal comparator (507) is connected to the output of the NAND gate element (505), which is configured to level shift the inverted pulse signal to a desired voltage level before sending the signal to the buffer circuit (303).

9. The system of claim 4, wherein the first and second signal comparators (502, 503) are powered by a positive power rail, wherein the power of the power rail is regulated by a low drop out linear voltage regulator, wherein noise on the power rails is reduced by a low pass filter.

10. The system of claim 4, wherein the adjustable delay elements (504, 506) comprise a coarse adjustable delay element and a fine adjustable delay element, wherein the coarse adjustable delay element comprises a large value resistor and a variable capacitor in a low pass filter configuration, wherein the fine adjustable delay element comprises a small value resistor and a variable capacitor in a low pass filter configuration (509), wherein each variable capacitor can be used to adjust a delay of the adjustable delay elements (504, 506).

11. The system of claim 10, wherein the fine adjustable delay element comprises a 500 Ohm resistor and a variable capacitor with a range of about 8 picoFarads to 45 picoFarads.

12. The system of claim 4, wherein the inverted pulse signal of the signal shaping circuit (302) sweeps with a rectangular pulse from −2.5V to +2.5V.

13. The system of claim 1, wherein the buffer circuit (303) comprises:
   a. a buffer comparator (406), configured to generate a positive version of an input pulse of the buffer circuit (303), wherein the input pulse is a pulse with minimum transmission line reflection received from the signal shaping circuit (302);
   b. a buffer comparator (402), configured to generate a negative version of the input pulse;
   c. a first inverter (403), connected to the first buffer comparator (406), which inverts the positive version of the input pulse; and
   d. a second inverter (404), connected to the second buffer comparator (402), which inverts the negative version of the input pulse;
   wherein a signal between the first and second inverter (403, 404) is a differential pulse, wherein the LED (409) is connected between the first and second inverter (403, 404), wherein the LED (409) is disposed such that the differential pulse first sweeps the LED (409) to a forward biased state, followed by a reverse biased state.

14. The system of claim 13, wherein buffer circuit (303) further comprises:
   a. a first plurality of inverters (403) connected in parallel to the first buffer comparator (406); and
   b. a second plurality of inverters (404) connected in parallel to the second buffer comparator (402);
   wherein the LED (409) is connected between the first plurality of inverters (403) and the second plurality of inverters (404), wherein each plurality of inverters (403, 404) are configured to switch at precisely the same time, wherein connecting each set of the plurality of inverters (403, 404) in parallel reduces the series (output) resistance of the buffer circuit (303).

15. The system of claim 14, wherein the first plurality of inverters (403) comprises about 16 inverters and the second plurality of inverters (404) comprises about 16 inverters, wherein a resistance of the driving circuit is about 4 Ohms.

16. The system of claim 13, wherein each plurality of inverters (403, 404) are implemented on a miniature logic chip to minimize the path of a current driving the LED (409).

17. The system of claim 13, wherein the first buffer comparator (406) and the second buffer comparator (402) are powered by positive and negative power rails, wherein a power of the positive and negative power rails is regulated by a low drop out linear voltage regulator, wherein noise on the positive and negative power rails is reduced by a low pass filter.

18. The system of claim 17, wherein power supply decoupling capacitors are placed across positive and negative power pins of the power rails, wherein an effective current path through the LED (409) is reduced to travelling from one decoupling capacitor through one inverter (403), through the LED (409), through the other inverter (404), to the other decoupling capacitor, wherein the reduction in high frequency current path decreases the parasitic inductance of the circuit, wherein the decrease in parasitic inductance decreases the LED intensity fall time of the circuit.

19. The system of claim 13, wherein the buffer circuit further comprises:
   a. a third buffer comparator (401), configured to receive a pulse using a terminated transmission line from the signal shaping circuit (302), before copying the pulse to the first and second buffer comparators (406, 402); and
   b. a fourth buffer comparator (405), configured to copy the output of the first buffer comparator, to provide a terminated transmission line synchronization signal output.

20. The system of claim 19, wherein the ADC (107) sampling is triggered by signal synchronized with the pulse of the LED via the synchronization signal output obtained from the buffer circuit (303).

* * * * *